US006713254B2

(12) United States Patent
Hakenbeck

(10) Patent No.: US 6,713,254 B2
(45) Date of Patent: *Mar. 30, 2004

(54) DNA PROBES, METHOD AND KIT FOR IDENTIFYING ANTIBIOTIC-RESISTANT STRAINS OF BACTERIA

(75) Inventor: Regine Hakenbeck, Fischbach (DE)

(73) Assignee: Max-Planck-Gesellschaft zur forderung der Wissenschaften E.V., Munich (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/403,609

(22) PCT Filed: Apr. 22, 1998

(86) PCT No.: PCT/DE98/01134

§ 371 (c)(1),
(2), (4) Date: Mar. 3, 2000

(87) PCT Pub. No.: WO98/48041

PCT Pub. Date: Oct. 29, 1998

(65) Prior Publication Data

US 2003/0087229 A1 May 8, 2003

(30) Foreign Application Priority Data

Apr. 24, 1997 (DE) .......................................... 197 17 346

(51) Int. Cl.[7] .................... C12Q 1/68; C07H 21/04; C07H 21/02
(52) U.S. Cl. .................... 435/6; 435/91.6; 536/23.2; 536/23.7; 536/24.32; 536/24.37
(58) Field of Search .................. 435/6, 91.6; 536/23.2, 536/23.7, 24.32, 24.37

(56) References Cited

U.S. PATENT DOCUMENTS 6,015,666 A * 1/2000 Springer et al. ............... 435/6

FOREIGN PATENT DOCUMENTS

| WO | 92 04458 | 3/1992 |
| WO | 96 08582 | 3/1996 |
| WO | WO 96/08582 | * 3/1996 |

OTHER PUBLICATIONS

Dowson et al. "Penicillin–resistant viridans streptococci have obtained altered penicillin–binding protein genes from penicillin–resistant strains of Streptococcus pneumoniae" Proc. Natl. Acad. Sci. USA, 1990, 87: 5858–5862.*

Grebe et al. "Penicillin–binding proteins 2b and 2x of Streptococcus pneumoniae are primary resistance determinants for differnet classes of beta–Lactam Antibiotics" Antimicrobial Agents and Chemotherapy, Apr. 1996: 829–834.*

Reichmann et al. "A global gene pool for high–level cephalosporin resistance in commensal Streptococcus species and Streptococcus pneumoniae" Journal of Infectious Diseases, 1997, 176: 1001–1012.*

Laible G. et al, "Interspecies recombinational events during the evolution of altered PBP2x genes in penicillin–resistant clinical isolates of Streptococcus penumoniae" Mol. Microbiol., Bd. 5, Nr. 8,—1991 Seiten 1993–2002, XP002084616.

Dowson C.G. et al, "Horizontal transfer of penicillin–binding protein genes in penicillin–resistant clinical isolates of Streptococcus pneumoniae" Proc. Natl. Acad. Sci. USA, Bd. 86,—Nov. 1989 Seiten 8842–8846, XP002084617.

* cited by examiner

Primary Examiner—Kenneth R. Horlick
Assistant Examiner—Cynthia Wilder
(74) Attorney, Agent, or Firm—Burns, Doane, Swecker & Mathis, L.L.P.

(57) ABSTRACT

The invention relates to a method for identifying antibiotic-resistant strains of bacteria, especially strains of *Streptococcus pneumoniae*. According to the invention, the method is based on a combination of hybridization experiments using sensitivity-specific and resistance-specific probes. The invention also relates to the DNA probes and to a kit for carrying out the inventive method.

12 Claims, 37 Drawing Sheets

Grid example of an oligonucleotide array

Figure 1:
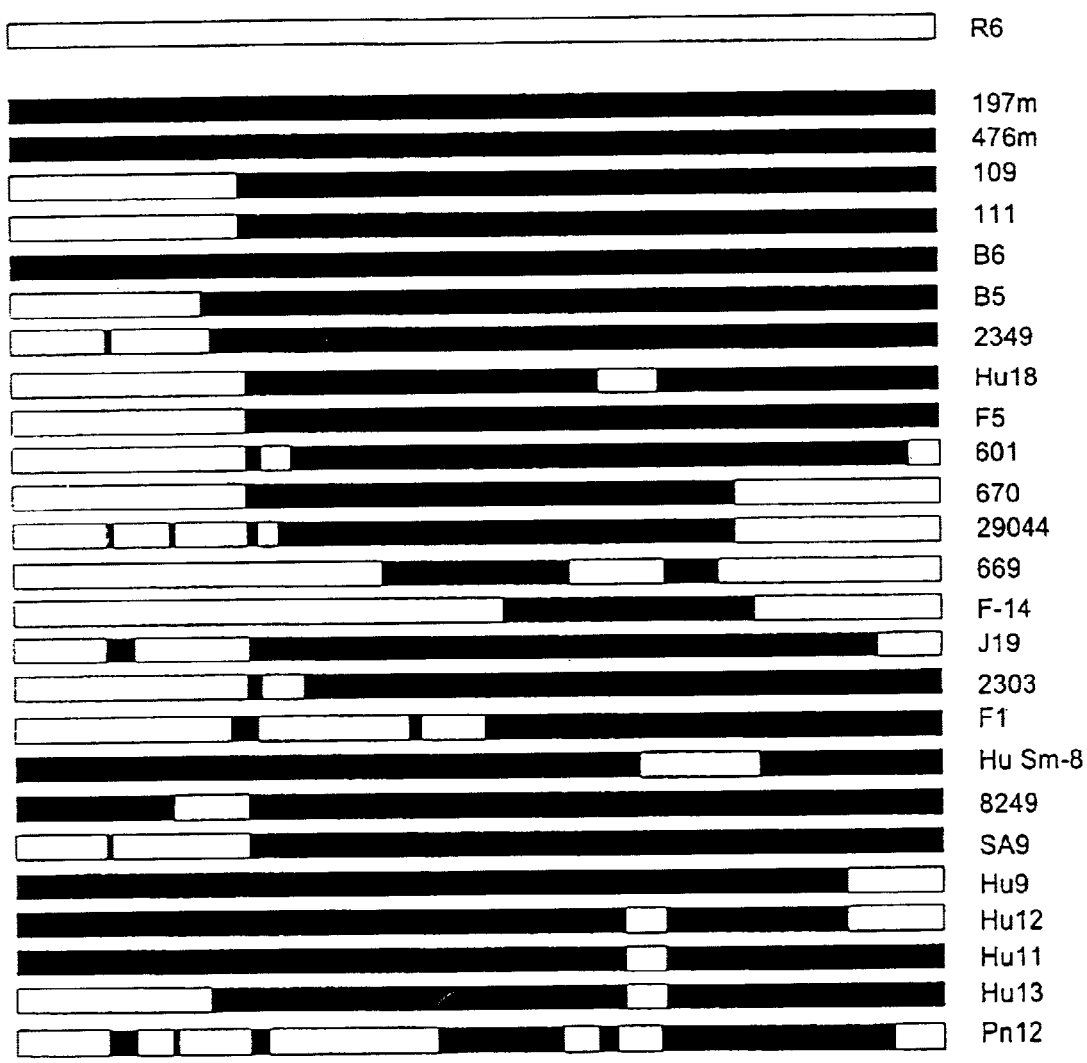

| 1 | 2 | 3 | 4 |
|---|---|---|---|
| 5 | 6 | 7 | 8 |
| I | II | III | IV |

A (R6 = sensitive)

| + | + | + | + |
|---|---|---|---|
| + | + | + | + |
| − | − | − | − |

B (2349 - resistant, globally occurring clone)

| + | − | − | − |
|---|---|---|---|
| − | − | − | − |
| + | + | + | + |

C (J19 - resistant)

| + | − | − | − |
|---|---|---|---|
| − | − | − | − |
| + | + | − | + |

D (Pn 12 - resistant, from Papua and unusual)

| + | − | + | + |
|---|---|---|---|
| − | − | − | − |
| − | − | − | − |

FIG. 2

FIG. 4A

R6-U5OR-197MIT-
476MIT-
B5MIT-2349-109-111NO-
U18-F5-601-670-29044-
M3-10712 (8-96)

Vertical strain-designating
numbers: first three numerals =
codon last numeral: 1, 2 or 3
position within the codon

```
                    0000000000000000000000000000000000000000000000111111111111
                    8888888888888888999999999999999999999999990000000000000000
                    5556667777888899990011112222333312312312312312312312312123
                    1231231231231231231231231231231231231231231231231231231231
         R6         GTCCCGATTGCTGAGGATGCAACCTCTTATAATGTCTATGCGGTCATTGATGAGAACTAT
         U5or       ..............-A---------------------------------------a-g-t-
         197MIT     ---T-----A----------G-T--G------A----------C-T----CA----C--C
         476MIT     --------------------G--A----------------------------------
         B5MIT      --------------------------C-------------------------------
         2349       --------------------------C-------------------------------
         109        --------------------------C-------------------------------
         111NO      -----A--------------------C-------------------------------
         U18        -----A----------------------------------------t-----------
         F5         -----A-----------------------------------------T----------
         601        -----A-----------------------------------------T----------
         670        -----A-----------------------------------------T----------
         29044      GTCCCGATTGCTGAGGATGCAACCTCTTATAATGTCTATGCGGTCATTGATGAACTAT
         R6         -G--T--C--A-----------------C-------------------A--A--C
         U11        -G--T--C--A------G----------C-----------T------A-A--A--C
         U13        -----A--------------------C-------------T-----------------
         U12        -G--T--C------G----------C-----------T--T-----A-A--A--C
         U9         -G--T-----A-----G-T--C---C-----------T--T-----A-A--A--C
         F1         --------------G--A-------C-----------T-------------
         669        -----A--------G--A-------C-----------T-------------
         F2         --------------G--A-------C-----------T-------------
         J19        --------------------------C-----------T-------------
         122        --------------------------C-----------T-------------
         2302       -----A---------------------C-------------T-----------C--T--A--A--C
         2303       -----A---------------------C-------------T-----------C--T--A--A--C
         8249       -----A---------------------C-------------T-T---------CA-A--A--C
         Sa9        --------C--------------------------------------t-----------
         Pn12       .....----ac---g----------c-------c--------t-t---a-a---C
         U8mit      ...G--T--C------G------------C-----------T-T----------a--A--A--C
         B6mit      --G--T--A-----G---------C-------------T-T--------C-T--A--A--C
         10712      --G--T--A-----G---------C-----------T-T--------A--A--C
         M3         --G--T--------G--T--C-----------------------T--A--A--C
```

FIG. 4B

FIG. 4C

```
                 1111111111111111111111111111111111111111111111111111111111111111
                 2222222222222222233333333333333333333333333333333344444444444444
                 5556666777788889999000011112222333312312312312312312222333444444
                 1231231231231231231231231231231231234455566677788899990011222333444
                 123123123123123123
       R6        GTCTTTCATAAGTATCTGGACATGAAGAATCCTATGTAAGAGACAACTCTCGCAACCT
       U5or      a-t--c-----ct---t--a-g--gagt--c--c-at--a-------A-----A
       197MIT    A-T-------------CT----T--T--G--GAGT--C--C-C--GA-----A-----A
       476MIT    A-T--C--------A----T-----G--G--T-----C-A----A--G--T--T-----A
       B5MIT     ------------------------------------------------------
       2349      ------------------------------------------------------
       109       ------------------------------------------------------
       111NO     ------------------------------------------------------
       U18       ---------------------------T--------------------------
       F5        ------------------------------------------------------
       601       ------------------------------------------------------
       670       ------------------------------------------------------
       29044     ------------------------------------------------------
       R6        GTCTTTCATAAGTATCTGGACATGAAGAATCCTATGTAAGAGAGCAACTCTCGCAACCT
       U11       ----C-----------T----T---G-T------G-A-------T-AG-T-----A
       U13       ----------------C-------------------------------------
       U12       ----C-----------T----T---G-T------G-A-------T-AG-T-----A
       U9        ----C----------T-A------G-T------G-A-------T-AG-T-----A
       F1        ------------------------------------------------------
       669       --------------------T-----------------------------T---
       F2        ------------------------------------------------------
       J19       ----C-------------------------------------------------
       122       ------------------------------------------------------
       2302      ------------------------------------------------------
       2303      ------------------------------------------------------
       8249      ----C-----------T----C--GG-T------T-A---A---T-G-T-----G
       Sa9       ----C-----------T----T---G-T------G-A-------T-AG-T-----A
       Pn12      ----C-----------T-A--T---G-T------G-A-------T-AG-T-----A
       U8mit     ----C-----------T----T---G-T------G-A-------T-AG-T-----A
       B6mit     ----C-----------T----T---G-T------G-A-------T-AG-T-----A
       10712     ----C-----------T-A--T---G-T------G-A-------T-AG-T-----A
       M3        ----C-----------T-A--T---G-T------G-A-------T-AG-T-----A
```

FIG. 4D

```
         1111111111111111111111111111111111111111111111111111111111111111111111111111111111111111111111
         4444444444445555555555555555555555555555555555555555555555555555555555555555666666666666666666
         5556666777788889999000011112222333344445555666677778888999900001111222233334444
         1231231231231231231231231231231231231231231231231231231231231231231231231231231231231231231231
R6       AATCTCAAGCAAGTTCCTTTGGAGCAAAGGGAAATGGGATTACCTATGCCAATATGATG
U5or     -------G-------------------T--T--A-----------------------t-
197MIT   -------A--G---------------TA-T-------------C----------C--A-
476MIT   G-----G--A--G--A--T-------------G-------------------------
B5MIT    ----------------------------TT-G-----C---------------------
2349     ----------------------------TT-G-----C---------------------
109      -----------------------------------------------------------
111NO    ---------------------------------C-------------------------
U18      -----------------------------------------------------------
F5       ---------------------------------C-------------------------
601      ---------------------------------C-------------------------
670      ---------------------------------C-------------------------
29044    ----------------------------TT-G-----C-----A---------------
R6       AATCTCAAGCAAGTTCCTTTGGAGCAAAGGGAAATGGGATTACCTATGCCAATATGATG
U11      ----A-CT------------------T--A-----------------------------
U13      -----------------------------------------------------------
U12      ---G-CC---G---------------T---------A----------------------
U9       ---G-CC-------------------T---T-----A----------------------
F1       --------------------------TT-G----------------------------
669      -----------------------------------------------------------
F2       --------------------------TT-G-------C---------------------
J19      --------------------------TT-G-------C---------------------
122      -----------------------------------------------------------
2302     ----------T---------------------------------A--------------
2303     ------------------------C-T--------------------------------
8249     ---G-CT-------------------TT-G-------C----A----------------
Sa9      ---G-CC-------------------T--------------A-----------------
Pn12     ---G-CC-------------------TT-G-------C-----A---------------
U8mit    ----G-CC-----G---------------T--------------A--------------C
B6mit    ----G-CC---------------------T--------------A--------------
10712    ----G-CC------T---------------------------A----------------
M3       ----G-CC---------------------T--------------A--------------
```

```
                    3333333333333333333333333333333333333333333333333333
                    00000000000000011111111111111111112222222222222222333333
                    55566677788899900111222331123123123123123123123123
                    123123123123123123123123123123123123
         ACGCAACGACCGACCTTTGATGCAGAGATACAAAAGAAGGCATTACAGAGGACTTTGTTTGG
R6       ------------------------------------------------------------
U5or     --C---------T------A---------------T-------A--C--T----------
197MIT   --C---------T------A---------------T-------A--C--T----------
476MIT   --C---------T------A---------------T-------A--C--T----------
B5MIT    --C---------T------A---------------T-------A--C--T----------
2349     --C---------T------A---------------T-------A--C--T----------
109      --C---------T------A---------------T-------A--C--T----------
111NO    --C---------T------A---------------T-------A--C--T----------
U18      --C---------T------A---------------T--G--T-A--C-------------
F5       --C---------T------A---------------T-------A--C--T----------
601      --C---------T------A---------------T-------A--C--T----------
670      --C---------T------A---------------T-------A--C--TA---------
29044    --C---------T------A---------------T-------A--C--T----------
R6       ACGCAACGACCGACCTTTGATGCAGAGATACAAAAGAAGGCATTACAGAGGACTTTGTTTGG
U11      --C---------T------A---------------T--G--T--C--CA-A---------
U13      --C---------T------A---------------T--G--T--C--CA-A---------
U12      --C---------T------A---------------T--G--T--C--CA-A---------
U9       --C---------T------A---------------T-------A--C--T----------
F1       ------------------------------A-----------------------------
669      --A---------------------------------------------------C-----
F2       ------------------------------------------------------------
J19      --C---------T------A----------T-----------T--G--T--C--CA-A--
122      --C---------T------A----------T-----------T--G--T--C--CA-A--
2302     ----GA------A------------C----TG----------T--G------AC---CA-
2303     ----GA------A------------C----------------T--G------AC---CA-
8249     ----GA------------------------------------T--G---GC-G--TA---
Sa9      ----GA------A------C----------------------T--G------A--C--TA
Pn12     ---------------------------------------------------------T--
U8mit    --C---------T------A---------------T----------A--C--T----G--
B6mit    --C---------T------A---------------T----------A--C--T-------
10712    --C---------T------A---------------T----------A--C--T-------
M3       --C---------T------A---------------T----------A--C--T-------
```

| | 3333333333333333333333333333333333333333333 |
|---|---|
| | 6666666666667777777777888888889999999999900000000001111111111222223333444 |
| | 5556667778889999991234567890123456789012345678901123456789012341234512312312 |
| | 123123123123123890012312312312312312323344234455667712312312312312312312312312 |
| | AAAATTGCAGATGCCACGATTCGAGATTGGGACGTTAATGAAGGATTGACTGGTGGCAGA |
| R6 | |
| U5OR | ----G--G------C---------------------------------T-----AC---T--T |
| 197MIT | ----G--G------C---------------------------------T-----AC---T--T |
| 476MIT | ----G--G------C---------------------------------T-----AC---T--T |
| B5MIT | ----A--G------C---------------------------------T-----AC---TG-G |
| 2349 | ----A--G------C---------------------------------T-----AC---TG-G |
| 109 | ----A--G------C-------------------------------T-T-----AC---TG-G |
| 111NO | ----A--G------C-------------------------------G-T-----AC---TG-G |
| U18 | ----A--G-TG---------------------------------------T-----AC---T--G |
| F5 | ----A--G------C---------------------------------T-----AC---TG-G |
| 601 | ----A--G------C-------------------------------CT-T-----AC---TG-G |
| 670 | ----A--G------C---------------------------------T-T-----AC---TG-G |
| 29044 | ----A--G-TG---------------------------------------T-T---GAC---TG-G |
| R6 | AAAATTGCAGATGCCACGATTCGAGATTGGGACGTTAATGAAGGATTGACTGGTGGCAGA |
| U11 | ----A--G-TG---------------------------------------T-----C---TG-T |
| U13 | ----A--G-TG---------------------------------------T-----C---TG-T |
| U12 | ----A--G-TG---------------------------------------T-----C---TG-T |
| U9 | ----A--G-TG---------------------------------------T-----C---TG-T |
| F1 | -------C-TT--T--C-----------A---C---------T-T-----C---TG-T |
| 669 | ----A--G--------------------C-----------T-----GAC---TG-G |
| F2 | -------G----------------------C---------------T-T------------ |
| J19 | ----A--G----------------------------------------T-T-----AC---TG-G |
| 122 | ----A--G----------------------------------------T-T-----AC---TG-G |
| 2302 | ----A--G----------------------------------------T-T-----AC---TG-G |
| 2303 | ----A--G----------------------------------------T-T-----AC---TG-G |
| 8249 | ----A--G-TG---------------------------------------GT-T-----GAC---T--G |
| Sa9 | ----A--G-TG---------------------------------------GT-T-----GAC---T--G |
| Pn12 | ---------------------------------------------------T-T------------ |
| U8mit | ----G--G-TG---------------------------------------T-----C---TG-T |
| B6mit | ----G--G-TG---------------------------------------GT-T-----AC---TG-G |
| 10712 | ----A--G----------------------------------------T--------C---TG-T |
| M3 | ----A--G----------------------------------------T-T-----AC---T--G |

FIG. 4P

```
            3333333333333333333333333333333344444444444444444
            8888888888888899999999999999999900000000000000000
            5556667778888999900001112222333344445555666777788889999000011112222333344
            123123123123123123123123123123123123123123123123123123123123123123123123
       R6   ATGATGACTTTTTCTCAAGGTTTTGCACACTCAAGTAACGTTGGGATGACCCTCCTTGAG
     U5or   ------------------------------------------------------------
   197MIT   -------C-TA------------C--T------C-------T------A------GT---A-----A
   476MIT   -------C-TA------------C--T------C-------T------A------GT---A-----A
    B5MIT   -------C-TA------------C--T------C-------T------A------GT---A-----A
     2349   -------C-TA------------C--T------C-------T------A------GT---A-----A
      109   -------C--A------------C--T------C-------T------A------GT---A-----A
    111NO   -------C-TA------------C--T------C-------T------A-C----GT---A-----A
      U18   -------C-TA------------C--T------C-------T------A------GT---A-----A
       F5   -------C-TA------------C--T------C-------T------A------GT---A-----A
      601   -------C-TA------------C--T------C-------T------A------GT---A-----A
      670   -------C-TA------------C--T------C-------T------A------GT---A-----A
    29044   -------C-TA------------C--T------C-------T------A------GT---A-----A
       R6   ATGATGACTTTTTCTCAAGGTTTTGCACACTCAAGTAACGTTGGGATGACCCTCCTTGAG
      U11   -------A------------G---T--------C-------T------C------TA---G-------
      U13   -------A------------G---T--------C-------T------C------TA---G-------
      U12   -------A------------G---T--------C-------T------C------TA---G-------
       U9   -------A------------G---T--------C-------T------C------TA---G-------
       F1   -------C------------------------------------------------------------
      669   -------------A-TA------------T---------------A------GT---A-----A
       F2   --------------------------------------------------------------------
      J19   -------C---A------------C--T------C-------T------A------GT---A-----A
      122   -------C---A------------C--TT-----C-------T------A------GT---A-----A
     2302   -------C-TA------------C--TT-----C-------T------A------GT---A-----A
     2303   -------C-TA------------C--T-T-----C-------T------A------GT---A-----A
     8249   -------C-TA------------C--T-T-----C-------T------A------GT---A-----A
      Sa9   -------C-TA------------C--T------C-------T------A------GT---A-----A
     Pn12   ---C-----G----------G---T-----------------------------------G--T---A
    U8mit   ---A------A---------G---T--------------------T----------GT---A-----A
    B6mit   -------A-------------A--T--------------------T----------GT---A-----A
    10712   -------------------------TA------------------TA----------A--T-----A
       M3   -------C--A------------C--T------C-------T------A------GT---A-----A
```

```
                    4444444444444444444444444444444444444444444444444
                    6666666666666666777777778888888888999999990000000011111111122222222333444
                    5556666777788889999000011112222333344445555666677778888999900001111222233 3444
                    1231231231231231231231231231231231231231231231231231231231231231231231231
R6              TTTACAGCTATTGCTAATGACGGTGTCATGCTGGAGCCTAAAATTTATTAGTGCCATTTAT
U5or            --------------------------------T--A--T-----------A-------T---
197MIT          --------------------------------T--A--T-----------A-------T---
476MIT          --------------------------------T--A--T-----------A-------T---
B5MIT           --------------------------------T--A--T-----------A-------T---
2349            --------------------------------T--A--T-----------A-------T---
109             --------------------------------T--A--T-----------A-------T---
111NO           --------------------------------T--A--T-----------A-------T---
U18             ----------C---------------------T--C--------------------------
F5              C-------------------------------T--A--T-----------A-------T---
601             --------------------------------T--A--T-----------------CG---T-G---
670             --------------------------------T--A--T-----------A-------T---
29044           C-------------------------------T--A--T-----------A-------T---
R6              TTTACAGCTATTGCTAATGACGGTGTCATGCTGGAGCCTAAAATTTATTAGTGCCATTTAT
U11             ----C---------------------------T--C--------------------------
U13             ----C---------------------------T--C--------------------------
U12             ----C---------------------------T--C--------------------------
U9              ----C---------------------------T--C-----------A--------------
F1              ----C---------------------------T--A--T-----------A-------T---
669             ----C---------------------------T--G--T--------A--A-----------
F2              ----C---------------------------T--G--T--------A--A-------CG---T-G---
J19             ----C---------------------------T--A--T--------A--A-------CG---T-G---
122             ----C---------------------------T--G--T--------A--A-------CG---T-G---
2302            ----C---------------------------T--G--T--------A--A-----------
2303            ----C---------------------------T--C-----------A--------------
8249            ----C---------------------------T--C-----------A--------------
Sa9             ----C---------------------------T--A-----------A--------------
Pn12            --C--G--------C-----------------T--A--T--------A--A-------CG---T-G---
U8mit           --C--G--------------------------T--A-----------A-----------------
B6mit           ----C---------------------------T--A--T-----------A-------T---
10712           ----C---------------------------T--C--------------A-------CG---T-G---
M3              --------------------------------T--A-----------A--------------
```

```
            5555555555555555555555555555555555555555555555555555555555555555555
            0000000000000011111111111111111111111111111111111122222222222222222
            5556667778889999000111222333444455566677788899900011122233312312323
            1231231231231231231231231231231231231231231231231231231231231231231
       R6   AAAGATGCAGCTAGTCTAACTCGGACTAACATGGTTTTGGTAGGACGGATCCGGTTTAT
       U5or ----G------A--CAC------A-A-C------A--C--A--T-----C--TC-A---
       197MIT ----G------A--CAC------A-A-C------A--C--A--T-----C--TC-A---
       476MIT ----G------A--CAC------A-A-C------A--C--A--T-----C--TC-A---
       B5MIT ----G------A--CAC------A-A-C------A--C--A--T-----C--TC-A---
       2349 ----G------A--CAC------A-A-C------A--C--A--T-----C--TC-A---
       109  ----G------A--CAC------A-A-C------A--C--A--T-----C--TC-A---
       111NO ----G------A--CAC------A-A-C------A--C--A--T-----C--TC-A---
       U18  -------------------C-----A----------------------------------
       F5   -------G------A--CAC------A-A-C------A--C--A--T-----C--TC-A---
       601  -------G------A--CAC------A-A-C------A--C--A--T-----C--TC-A---
       670  -------G------A--CAC------A-A-C------A--C--A--T-----C--TC-A---
       29044 G------A--CT-G------T-------A-A--A--A--T-----C--TA-A---
       R6   AAAGATGCAGCTAGTCTAACTCGGACTAACATGGTTTTGGTAGGACGGATCCGGTTTAT
       U11  ------------C-A------T--C-A------C----------A----------
       U13  ------------C-A------T--C-A------C----------A----------
       U12  ------------C-A------T--C-A------C----------A----------
       U9   G------A--CT-G--A----T------C-------A-A--A--T-----C--TC-A---
       F1   -------G--C-A------T------C-------A------------------A----
       669  ------------------------T--A------------------------TAGA---
       F2   ------A--G--ATCAG-C--G--TGACC-T------A----T-A--A--C--TACA---
       J19  G------A--CT-G------T-------A-A--A--A--T-----C--TC-A---
       122  G------A--CT-G------T-------A-A--A--A--T-----C--TC-A---
       2302 ------------C-A------T------C-------A----------TAGA---
       2303 ------------C-A------T------C-------A----------TAGA---
       8249 ------------C-A------T------C-------A----------TAGA---
       Sa9  ------------C--------T------C-------A----------TAGA---
       Pn12 ------------C-A------T------C-------A------A-C-T-C--A--A---
       U8mit ------G---CT-G--G--A--GC-T------A--C--T-----C--TC-A---
       B6mit G------A--A--CT-G------T------A-A--A--A--T-----TAGA---
       10712 ------------C-A------T------C-------A----------TC-A---
       M3   G------A--CT-G------T-------A-A--A--A--T-----C--TC-A---
```

```
                  5555555555555555555555555555555555555555555555555555555555555
                  6666666666666777777777777777777777777777777777788888888888888
                  5556677788899900011122223333444455556666777788899900011222333444
                  1231231231231231231231231231231231231231231231231231231231231231 23
R6                TTAACCGACTATATTTTCTCGGCTGTATCGATGAGTCCGGCTGAAATCCTGATTTTATC
U5OR              -CT----A-T---------------A-T---GA-T-----A-T-----------T---
197MIT            -CT----A-T---------------A-T---GA-T-----A-T-----------T---
476MIT            -CT----A-T---------------A-T---GA-T-----A-T-----------T---
B5MIT             -CT----A-T---------------A------GA-T-----A-T-----------T---
2349              -CT----A-T---------------A-T---GA-T-----A-T-----------T---
109               -CT----A-T---------------A-T---GA-T-----A-T-----------T---
111NO             -CT----A-T---------------A-T---GA-T-----A-T-----------T---
U18               -CT----A---------C-------T-----G-T-----A-T-----------T---
F5                -CT----A-T---------------A-T---GA-T-----A-T-----------T---
601               -CT----A-T---------------T-----GA-T-----AC-T-----------T---
670               -CT----A-T---------------A-T---GA-T-----A-T-----------T---
29044             -CT----A-T---------------A-T---GA-T-----A-T-----------T---
R6                TTAACCGACTATATTTTCTCGGCTGTATCGATGAGTCCGGCTGAAAATCCTGATTTTATC
U11               CCT----A------C----------T-----G-T---AC--T---------------
U13               CCT----A------C----------T-----G-T---AC--T---------------
U12               -CT----A-T---------------ATTGC-GA-T--C-A-----T---------------
U9                -CT----A-T---------------A-T---GA-T-----A-T-----------T---
F1                -CT----A--A-C------------A-T---GG-T---AC--T------C---------
669               -CT---TA--A-C------------T-----G-C---AC--T-----------T---
F2                -C----AA--A-C------------A-T----T-----CAC--A---G-----------
J19               -CT----A------C----------A-T-----T-----GA-T-----A-T-----------T---
122               -CT----A------C----------T-----T-----GA-T-----A-T-----------T---
2302              -CT----A------C----------T-----G-T---AC--T-----------T---
2303              -CT----A------C----------T-----T-----GA-T-----A-T-----------T---
8249              GC---GA-T--C----A--T--A-T-----A---TA-GG---G------C---------
Sa9               GC---GA-T--C----A--T--A-T-----A-------A---C--G------C---------
Pn12              ACG---A-T--C---------T---------A-----------A------A---------
U8mit             ------------T--------------------A----------A-----------------
B6mit             -CT----A-T---------------A-T---GA-T-----A-T-----------T---
10712             -CT------A---C----------T-----T--GG-T---AC--T---------
M3                -CT----A-T---------------A-T---GA-T-----A-T-----------T---
```

```
                    7777777777777777777
                    4444444444444444555
                    5556667778889999000
                    1231231231231231231231231231 23
                    ACATTAACTTTAGGAGAC
R6                  
U5or                -A----------------
197MIT              -A----------------
476MIT              -A----------------
B5MIT               ------------------
2349                -A----------------
109                 -A----------------
111NO               ------------------
U18                 -A----------------
F5                  -A----------------
601                 ------------------
670                 ------------------
29044               ------------------
R6                  ACATTAACTTTAGGAGAC
U11                 -A-----C----------
U13                 -A----------------
U12                 -A----------------
U9                  TACA--------------
F1                  -A----------------
669                 ------------------
F2                  ------------------
J19                 ------------G-----
122                 ------------------
2302                -A----------------
2303                -A----------------
8249                -A----------------
Sa9                 -A----------------
Pn12                ------------------
U8mit               -A----------------
B6mit               -A----------------
10712               CA----------------
M3                  -A-------------T--
```

DNA PROBES, METHOD AND KIT FOR IDENTIFYING ANTIBIOTIC-RESISTANT STRAINS OF BACTERIA

This application is a national stage filing under 35 U.S.C. §371 of International Application No. PCT/DE98/01134 filed on Apr. 22, 1998.

The present invention relates to DNA probes, a method and a kit for identifying antibiotic-resistant strains of bacteria.

The occurrence of antibiotic-resistant strains of bacteria, particularly of streptococcus strains, represents an increasing problem. So far, antibiotic susceptibility tests have been carried out by isolating bacteria and establishing a culture to define the minimum antibiotic inhibitory concentration in a biological test. This method takes at least 1 to 2 days. Well-calculated and thus optimum treatment is not possible within this period. Therefore, there is a need for a faster identification of existing resistances.

The object of the present invention consists in providing products and methods by means of which bacterial strains, particularly streptococcus strains, can be tested fast and reliably for existing antibiotic resistances.

This object is achieved by the subject matters defined in the claims.

The invention is described below by way of penicillin resistance of *Streptococcus pneumoniae*. However, this principle also applies in correspondingly general fashion to bacteria and resistances to other antibiotics. Neisserias and MRSA strains (methicillin-resistant *Staphylococcus aureus*), which do not produce β-lactamase, are mentioned by way of example.

All of the penicillin-resistant *S. pneumoniae* strains have modified penicillin target proteins (penicillin-binding proteins, PBP). The DNA sequences of genes which play a decisive part in the development of penicillin resistance in *Streptococcus pneumoniae* have meanwhile been determined in a number of penicillin-resistant streptococcus strains. Three genes were identified where differences between sensitive and resistant strains occur in connection with the development of penicillin resistance: PBP2x, PBP1a and PBP2b.

A comparison between the DNA sequences shows within the genes regions which are present in all of the sensitive *S. penumoniae* strains but are modified in resistant strains. In this connection, reference is made to FIG. 1 which shows that the resistant strains differ more or less markedly from the sensitive strain R6 in the PBP2x gene but also differ among themselves.

Because of the above finding that differences between penicillin-sensitive and penicillin-resistant strains occur within certain genes, the applicant developed DNA probes by means of which resistant and sensitive strains can be differentiated. In this connection, reference is made to FIG. 4. The probes which are specific to sensitive sequences discriminate genes which code for low-affinity PBP variants responsible for penicillin resistance. The probes which are specific to resistant sequences react with a very frequently occurring class of PBP variants and can also be used for epidemiological purposes.

The applicant identified the following DNA probes [SEQ ID NOS.:1–8]:

a) Sensitivity-specific probes for PBP2x. The numerals in the column "nucleotide" refer to the nucleotides of the published sequence (Laible et al., Mol. Microbiol. 5, pp. 1993–2002 (1991)). The numerals in parentheses refer to the codon and the position (1, 2 or 3) within the codon of the structural gene. The number of bases in the nucleotide is given by "meric".

| Nucleotide (codon) | oligonucleotide | -meric |
|---|---|---|
| 314–330 (105.2–110.3) | AGT CAG CAA CGG GTA AG | (1) 17 |
| 758–774 (253.2–258.3) | AAC GAA CGA TGG ACG GT | (2) 17 |
| 792–809 (264.3–270.2) | CAT TTC CAG NCC CCT CCA | (3) 18 (N: preferably C) |
| 1098–1114 (366.3–372.1) | TGC AGA TGC CAC GAT TC | (4) 17 |
| 1302–1317 (434.2–439.3) | CTG GTC AGC TTC CTG CG | (5) 17 |
| 1677–1696 (559.3–566.1) | TGG TTA TCT AGT CGG GTT AA | (6) 20 |
| 1715–1731 (572.2–577.3) | CTG TAT CGA TGA GTC CG | (7) 17 |
| 2011–2029 (671.1–677.1) | AAC AGT TCT GCT GAA GAA G | (8) 19 | b) Resistance-specific probes [SEQ ID NOS.: 14–17] for PB2x (as above; sequences in parentheses [SEQ ID NOS.: 20–23] are in accordance with the corresponding sections of sensitive strains).

```
 1065-1084    (AGG AGA AGT CTT TAA TAG T)
(355.3-361.3)  TGG AGA ATA NTT CAA TAG N    (I)     19 (N: preferably C)

1202-1221    (CCC TCC TTG AGC AAA AGA TG)
(401.2-407.3)  GTC TAC TTG AAC AAA AAA TG   (II)    20

1549-1566    (TTG GTA GGG ACG GAT CCG)
(517.1-522.3)  TTA GTT GGG ACG GAC CCT      (III)   18

1759-1776    (GTG ACG GTC CAA CAA CCT)
(587.1-592.3)  GTA ACN NTT CAA CAG CCT      (IV)    18 (N: preferably G)
``` c) Sensitivity-specific probes [SEQ ID NOS.: 9–12] for PBP1a (values refer to the nucleotides of the published sequence of the structural gene; Martin et al., EMBO J. 11, pp. 3831–3836 (1992))

```
(1034-1051) TAG GAG CAC GCC ATC AGT                18
            (specific in most known sequences)

1631-1648  GAC GAA ATG CCT ATC TTG                18

1722-1740  CTC TCA ATT TGT AGC ACC T              19

1794-1812  CTA TTC TAA CCG TCT GAC A              19
``` d) Resistant specific probes [SEQ ID NOS.: 18–19] for PBP1a ([SEQ ID NOS.: 24–25] in parentheses).

```
            (TAC AGA CGA ATA CGT TGC C)
945-963      CTC CGA NCA ATA CGT CTC T     19 (N: preferably T)

(GCA CCT GAT GAA CTA TTT GC)
1735-1754    GCT CCA GAT NAA ATG TTT GT    20 (N: preferably G)
``` e) Sensitivity-specific probes [SEQ ID NO.: 13] for PBP2b (values refer to the nucleotides of the published sequence of the structural gene; Hakenbeck, R., Matrin, C., Dowsen, C., Grebe, T., J. Bacteriol. 176, pp. 5574–5577 (1996))

```
 1329-1348    ATC AAA TAC CTA TAT GGT CC       20
```

N=any nucleotide

The above probes and those differing therefrom by one or several nucleotides, preferably up to 4 nucleotides, respectively, are perfectly suited to test unknown *Streptococcus pneumoniae* strains for resistance to penicillin.

For this purpose, bacteria according to the invention are centrifuged off a sample and in the case of *S. pneumoniae* the PBP genes (the resistance determinants) are amplified directly via PCR (polymerase chain reaction) as described in the literature (Grebe and Hakenbeck (1996), Antimicrob. Agents Chemother. 40, pp. 829–834). The advantage in connection with *S. pneumoniae* consists in that a detergence-induced lysis occurs rapidly and thus PCR can be carried out without long-winding DNA preparations. Since this step fails with other streptococci, only pneumococcus DNA is amplified specifically by means of this step. As an alternative, bacterial DNA (chromosomal and/or extrachromosomal) is isolated according to standard methods. This DNA is hybridized with at least one sensitivity-specific probe and with at least one resistance-specific probe under standard conditions with which a person skilled in the art is sufficiently familiar (see e.g. Maniatis et al., Molecular Cloning, Cold Spring Harbor, N.Y.: Cold Spring Harbor Laboratory). The hybridization is preferably carried out under stringent conditions such as 20° C. below the melting point of the hybridizing DNA. The oligonucleotides are preferably chosen such that they have similar melting temperatures and thus several of them can be tested in the same hybridization batch under the same conditions (see FIG. 2). The oligonucleotides are preferably labeled when offered ($P^{32}$, $S^{35}$, biotin/avidin system; dioxygenine (DIG)-labeled; fluorescein-labeled) and hybridized against immobilized DNA. As an alternative, the oligonucleotides are offered on an oligonucleotide microarray in non-labeled fashion and the DNA to be hybridized is obtained via PCR and labeled while amplified.

It can be concluded from the hybridization result whether or not the unknown strain is sensitive to antibiotics. Depending on the resistance gene, at least one sensitivity-specific probe and one resistance-specific probe should be used for the hybridization. However, the DNA of the unknown strain is hybridized advantageously with several sensitivity-specific and resistance-specific probes in succession, since evaluation of resistance by means of only one combination of sensitivity-specific probes and resistance-specific probes can be inaccurate and rather only serve as a rough estimate. This applies particularly to the case of penicillin resistances in pneumococci and neisserias.

Preferred hybridization conditions depend on the AT content and length of the oligonucleotides. The person skilled in the art can select suitable conditions on the basis of his technical knowledge. Thus, e.g. 10–100 ng/ml labeled oligonucleotide for PBP2x (see above) are used in SSC hybridization solution at a hybridization temperature of 45°–60° C. for at least 5 hours, preferably overnight.

Figure 3:
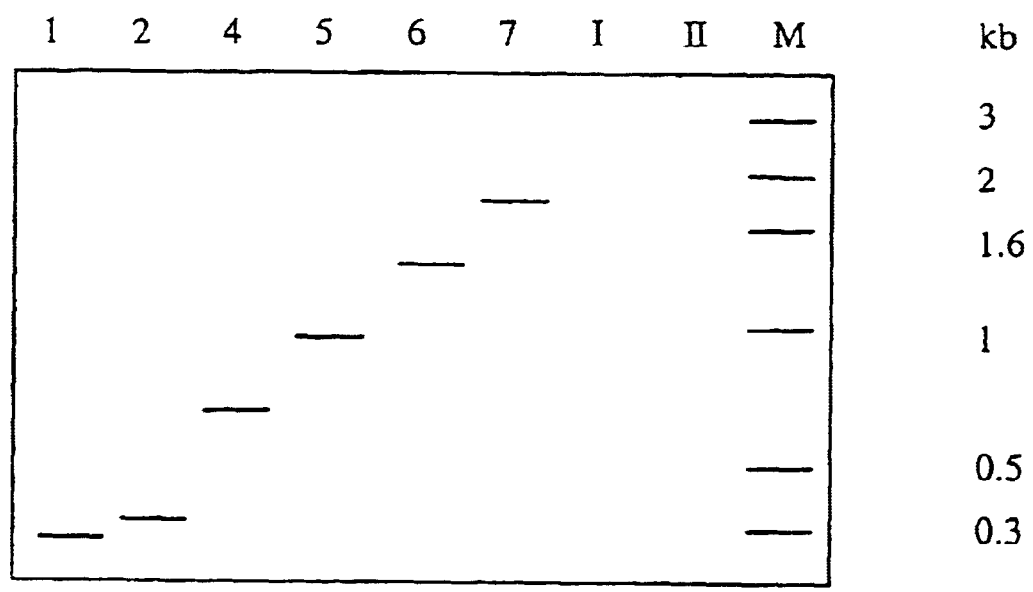

The oligonucleotides can also be used as PCR primers to as to develop a PCR test therewith (see FIG. 3). This test can dispense with the somewhat more time-consuming hybridization. However, several PCRs must be used per strain. This method is suitable above all for epidemiological purposes.

The circumstance that less probes are known for PBP1a and particularly for PBP2b follows from the fact that smaller gene regions are of significance for resistance in PBP1a and particularly in PBP2b and therefore also only smaller regions have a sequence variation.

The invention also relates to a kit for carrying out the above method. This kit comprises means for isolating DNA from bacteria and for the PCR amplification of specific resistance determinants, respectively, sensitivity-specific DNA probes and resistance-specific DNA probes (lyophilized and as oligonucleotide microarray, respectively), reagents, solutions, buffers and means for hybridization and the subsequent detection of hybridized DNA. The sensitivity-specific DNA probes and resistance-specific DNA probes are preferably the ones listed above.

The advantage of the present invention is that bacteria, particularly pneumococci, can be assessed as to antibiotic resistance within the shortest time, i.e. within few hours. This enables subsequently a well-calculated and efficient treatment of diseased patients.

The invention is further described by means of the figures showing:

FIG. 1 shows a comparison of gene sections of the Streptococcus pneumoniae PBP2x gene between penicillin-sensitive and penicillin-resistant strains; codon 85–750 R6: penicillin-sensitive strain Others: penicillin-resistant strains FIG. 2 shows the hybridization on an oligonucleotide array The arrangement of the probes on the array is indicated in the first block of the figure. Numerals (1) to (8) and (I) to (IV), respectively, correspond to the numbering of the above-mentioned probes for PBP2x.

A) Strain R6, a sensitive S. pneumoniae laboratory strain and representative of other sensitive strains: all sensitivity-specific oligonucleotides (Nos. 1–8) are identified whereas all of the four resistance-specific oligonucleotides (I–IV) are not identified.

B) Strain 2349 whose PBP2x gene belongs to a frequently and globally occurring class of PBP2x genes of resistant pneumococci. Only one of the sensitivity-specific oligonucleotides is identified, since the modified sequence does not cover the 3' region of the gene. All of the other sensitivity-specific oligonucleotides (Nos. 2–8) do not hybridize. All of the resistance-specific oligonucleotides (I–IV) hybridize.

C) Strain J19, a resistant strain having a PBP2x which only in part has sequences which correspond with that of strain. 2349. One of the resistance-specific oligonucleotides (III) does not respond.

D) Strain Pn12, a resistant strain from Papua, whose PBP2x has an unusual sequence. Five of the sensitivity-specific oligonucleotides do not respond, an evidence for the fact that the PBP2x has no continuous sensitive sequence (and thus conveys resistance). However, the resistance-specific oligonucleotides do not respond either, which indicates that an unusual sequence is also present in the "resistant" gene region. Strains like this one are an exception but can be detected clearly on account of screening, above all when further oligonucleotides are used which are specific to other PBPs.

FIG. 3 shows the result of PCR reactions for the amplification of S. pneumoniae R6 DNA as an application on a agarose gel. The PCR primers used were the above PBP2x probes marked above by (1) to (7) as forward primers and probe (8) as reverse primer each. PCRs having probes (I) as forward primer as well as (IV) as reverse primer and (II) as forward primer as well as (IV) as reverse primer, respectively, were carried out as a control. M=size marker. It can be clearly identified that on the gel shown only the sensitivity-specific probes result in an amplification whereas none takes place with resistance-specific probes.

Figure 4B:
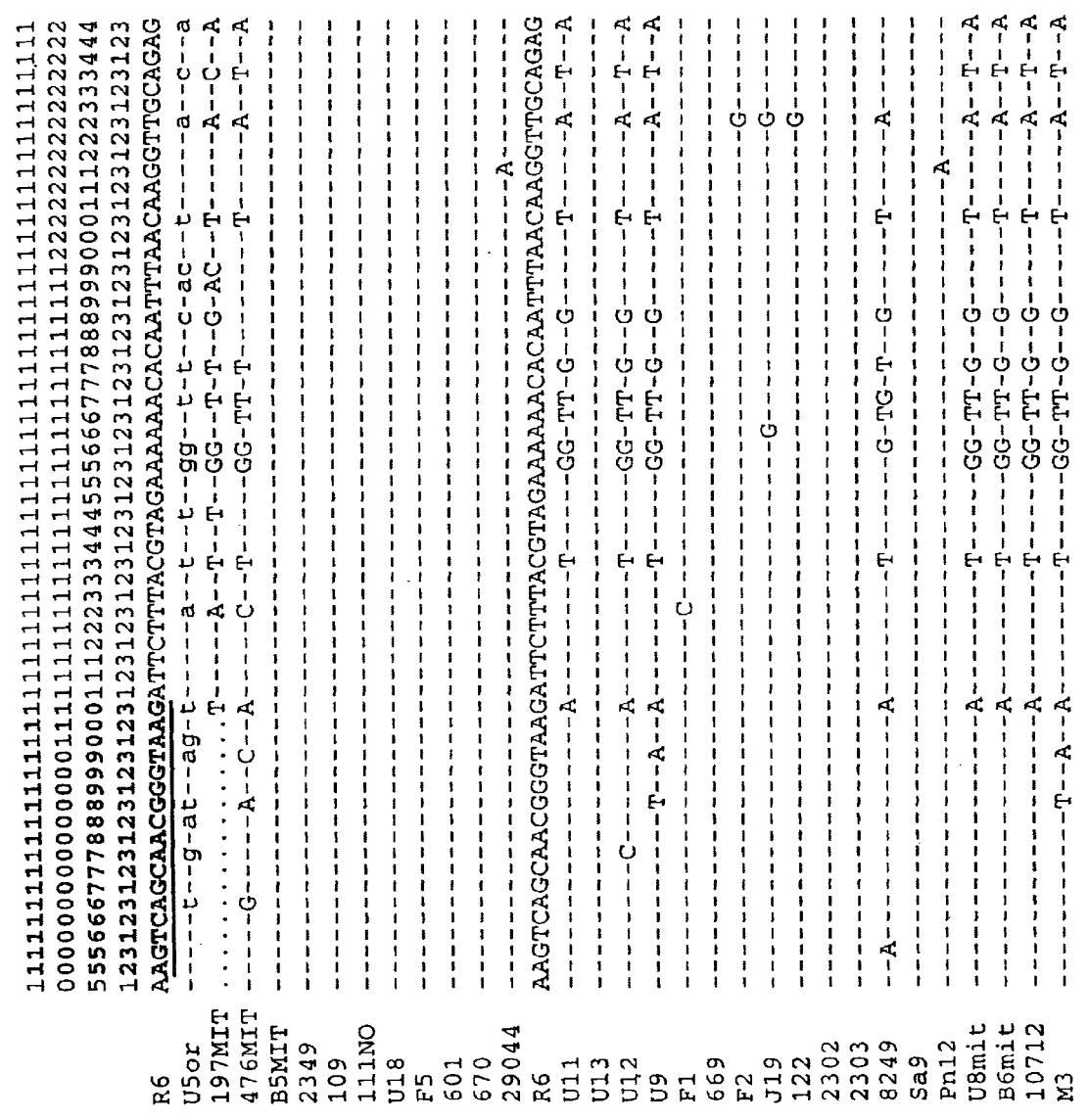
Figure 4E:
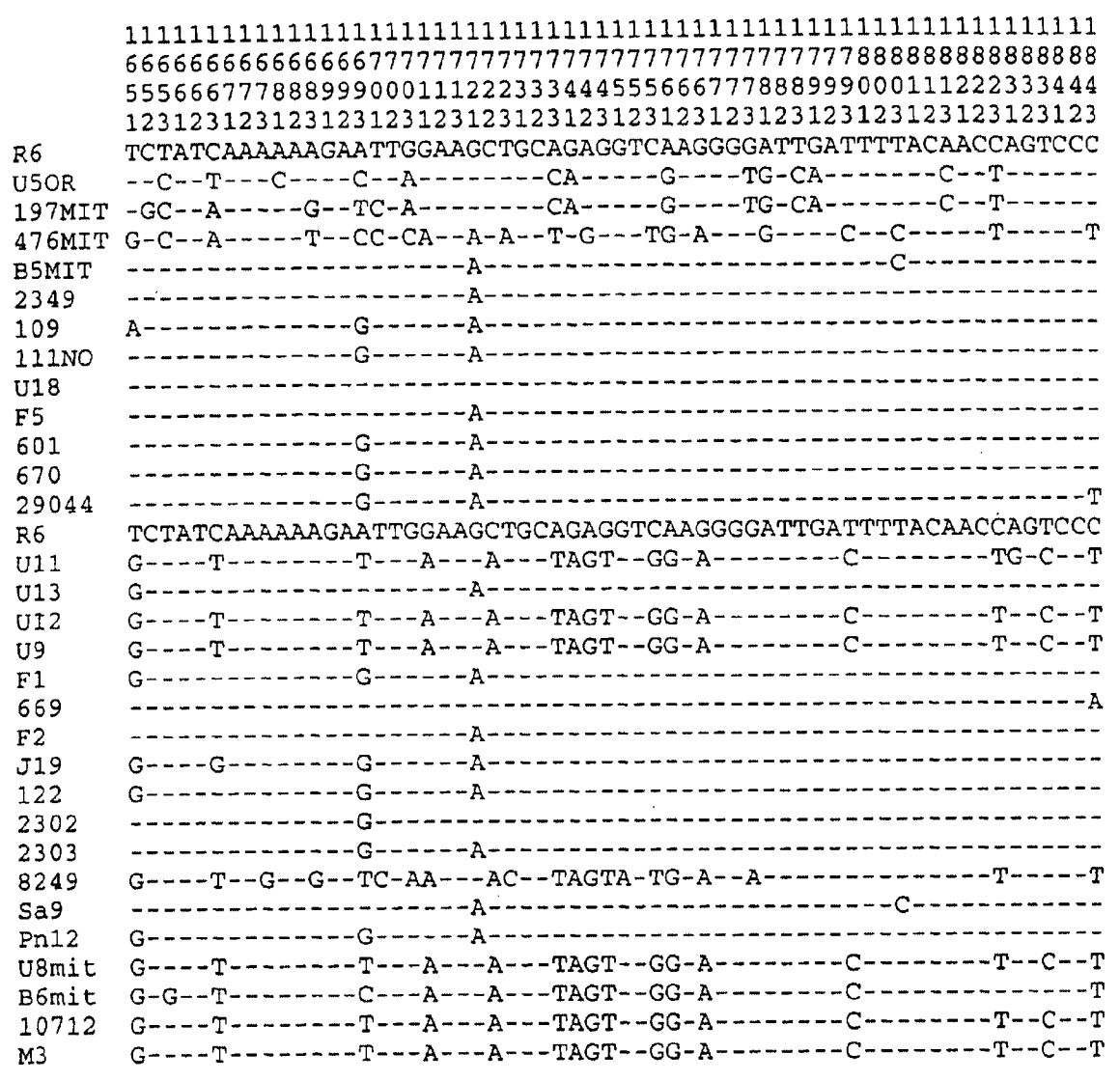
Figure 4F:
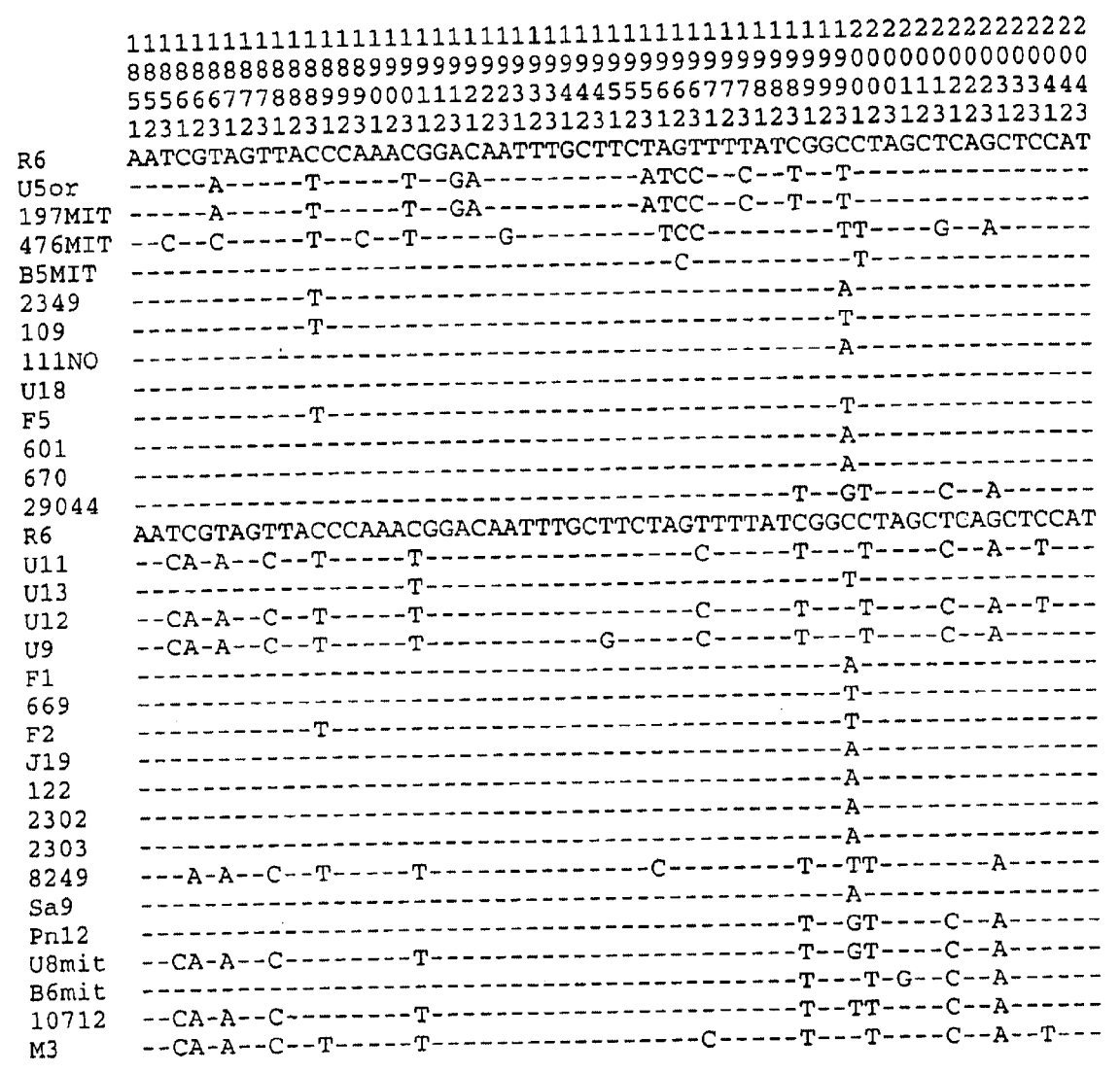
Figure 4G:
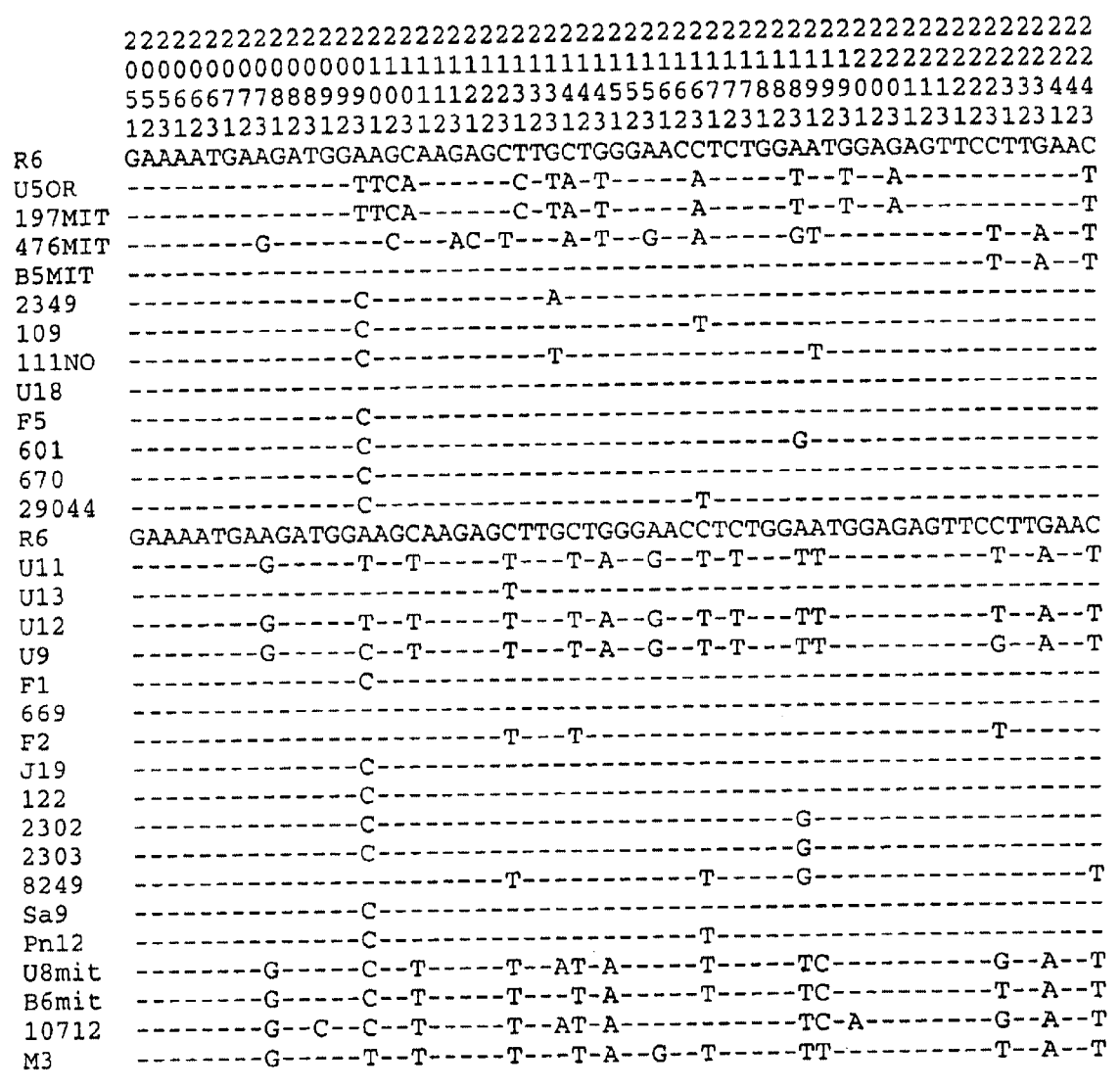
Figure 4H:
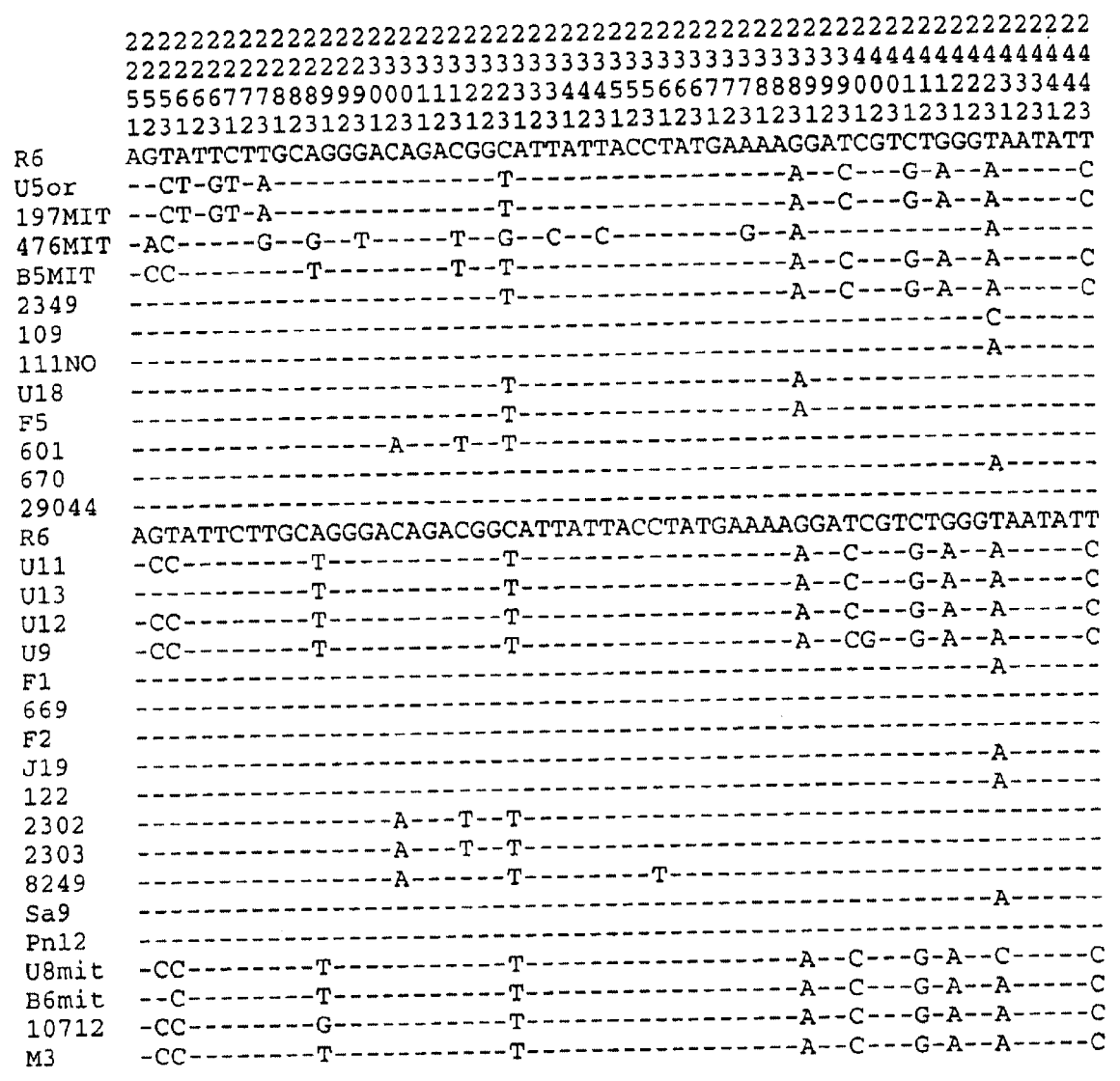
Figure 4J:
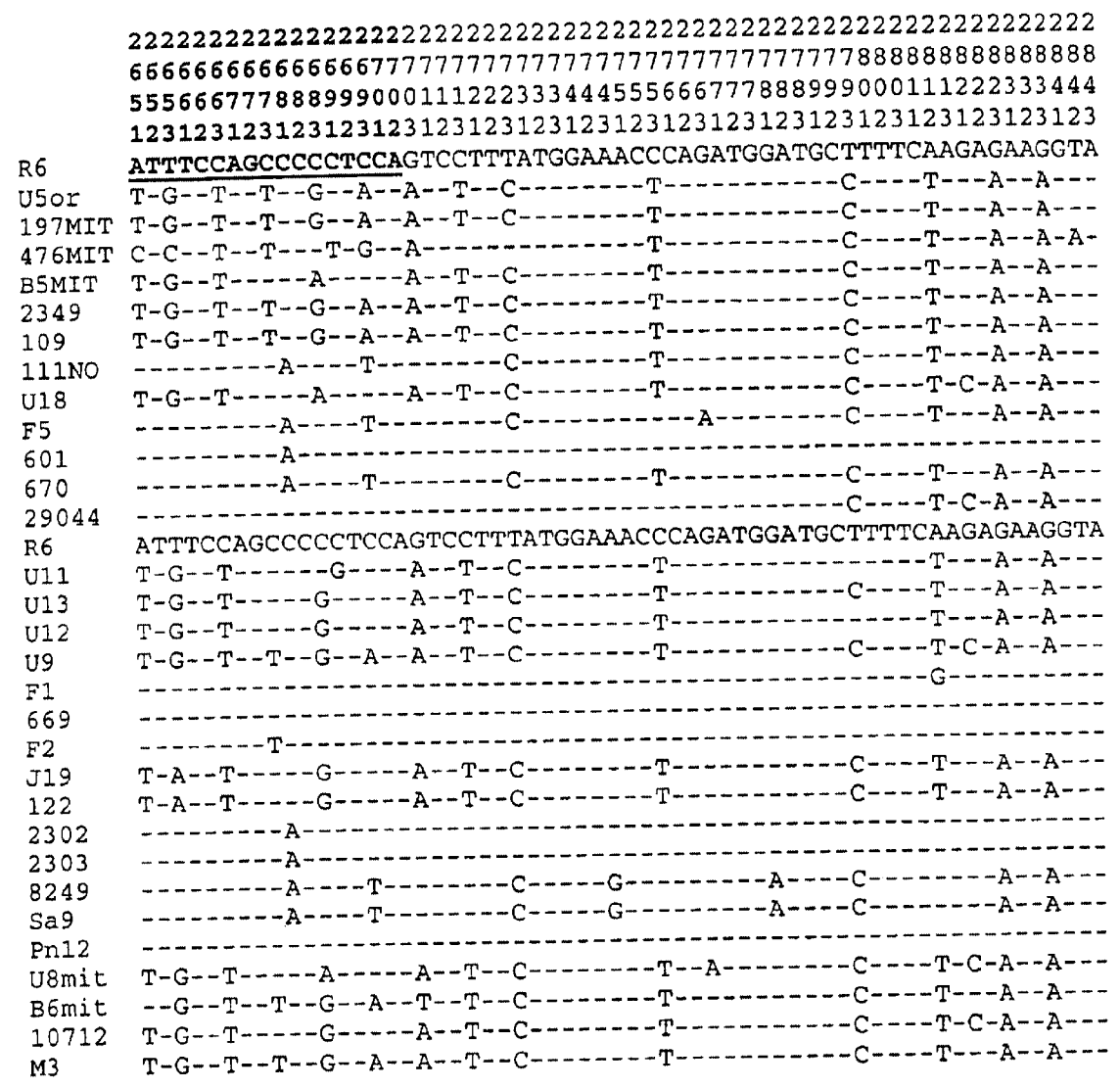
Figure 4K:
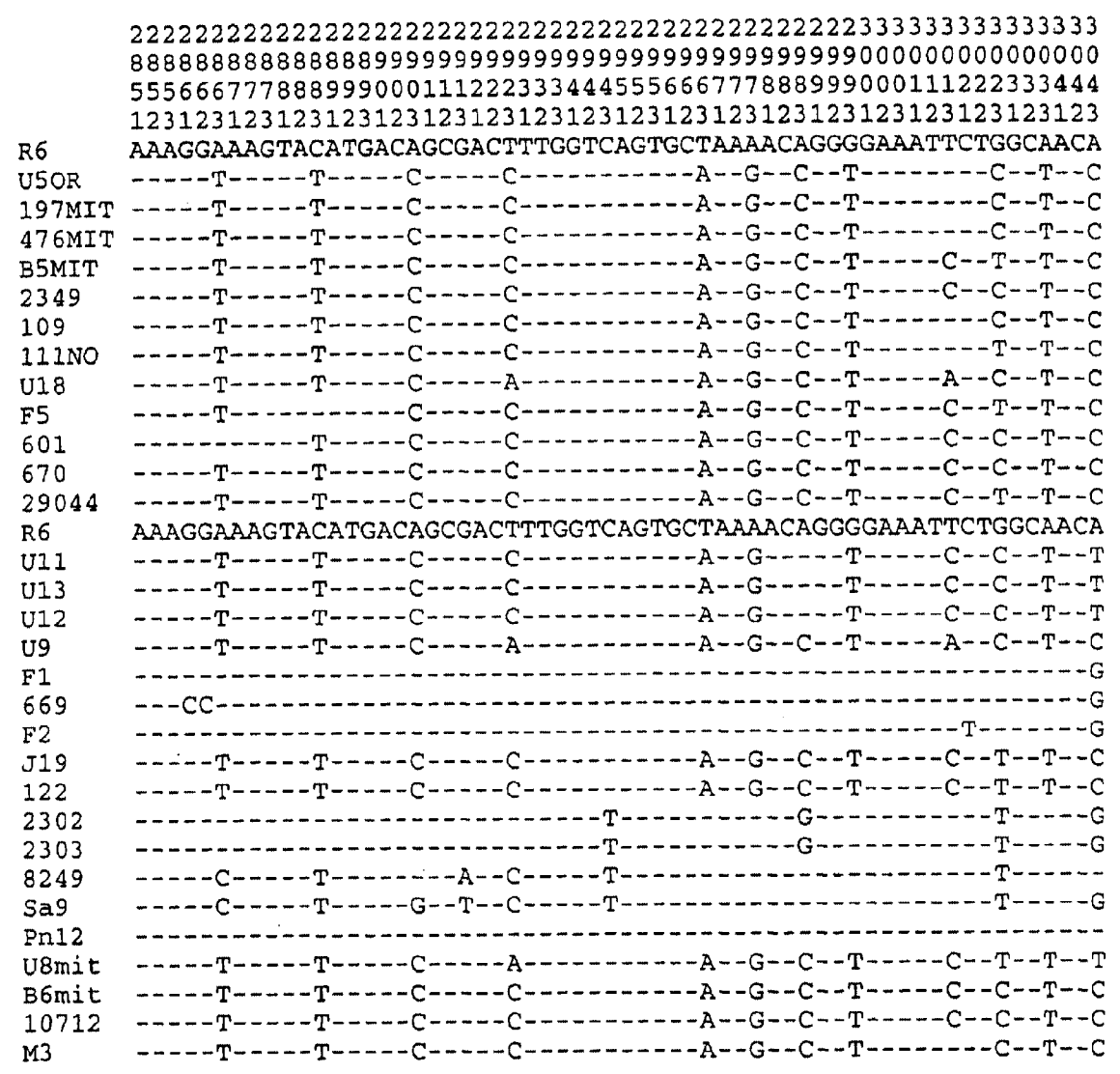
Figure 4M:
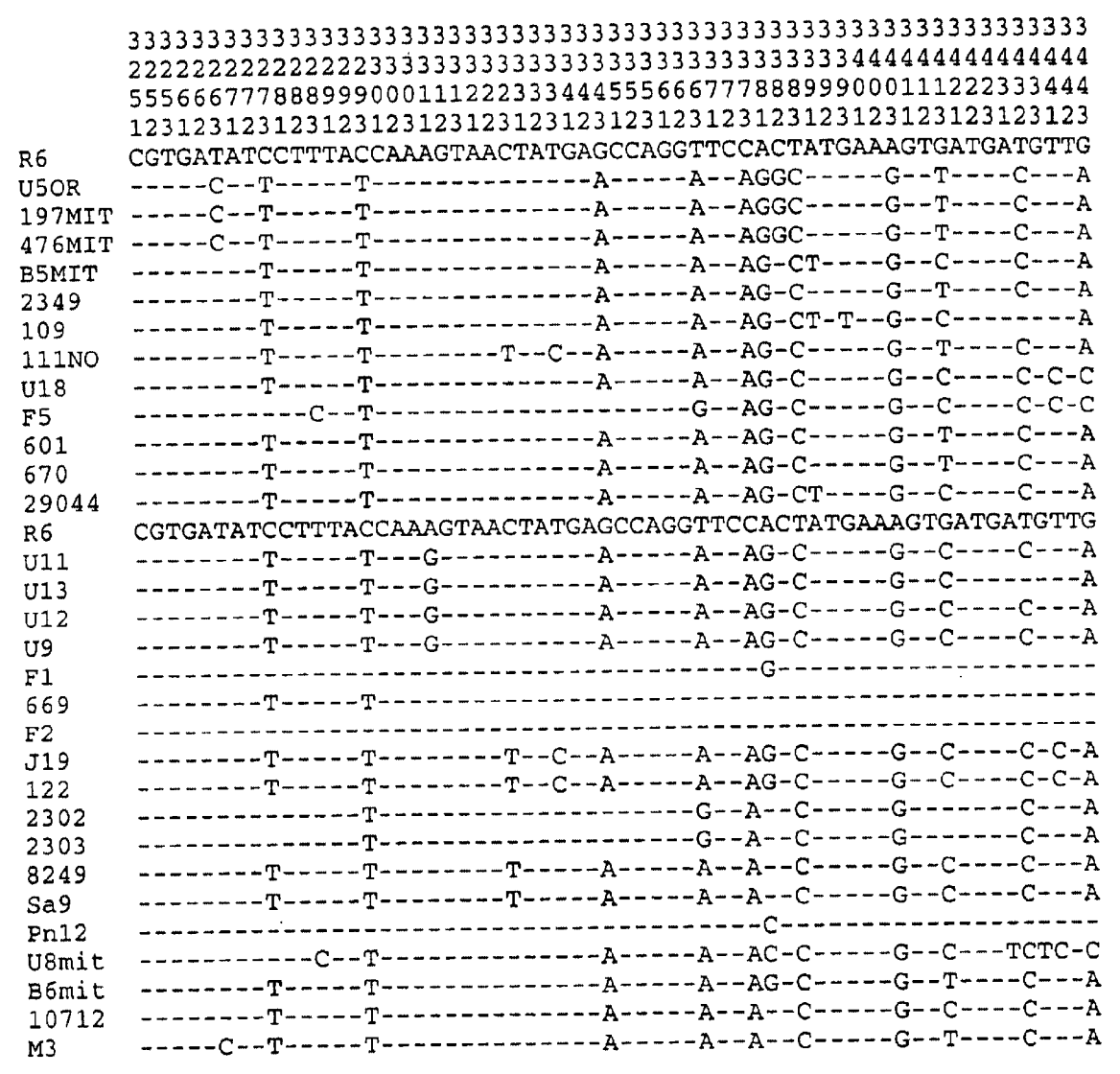
Figure 4N:
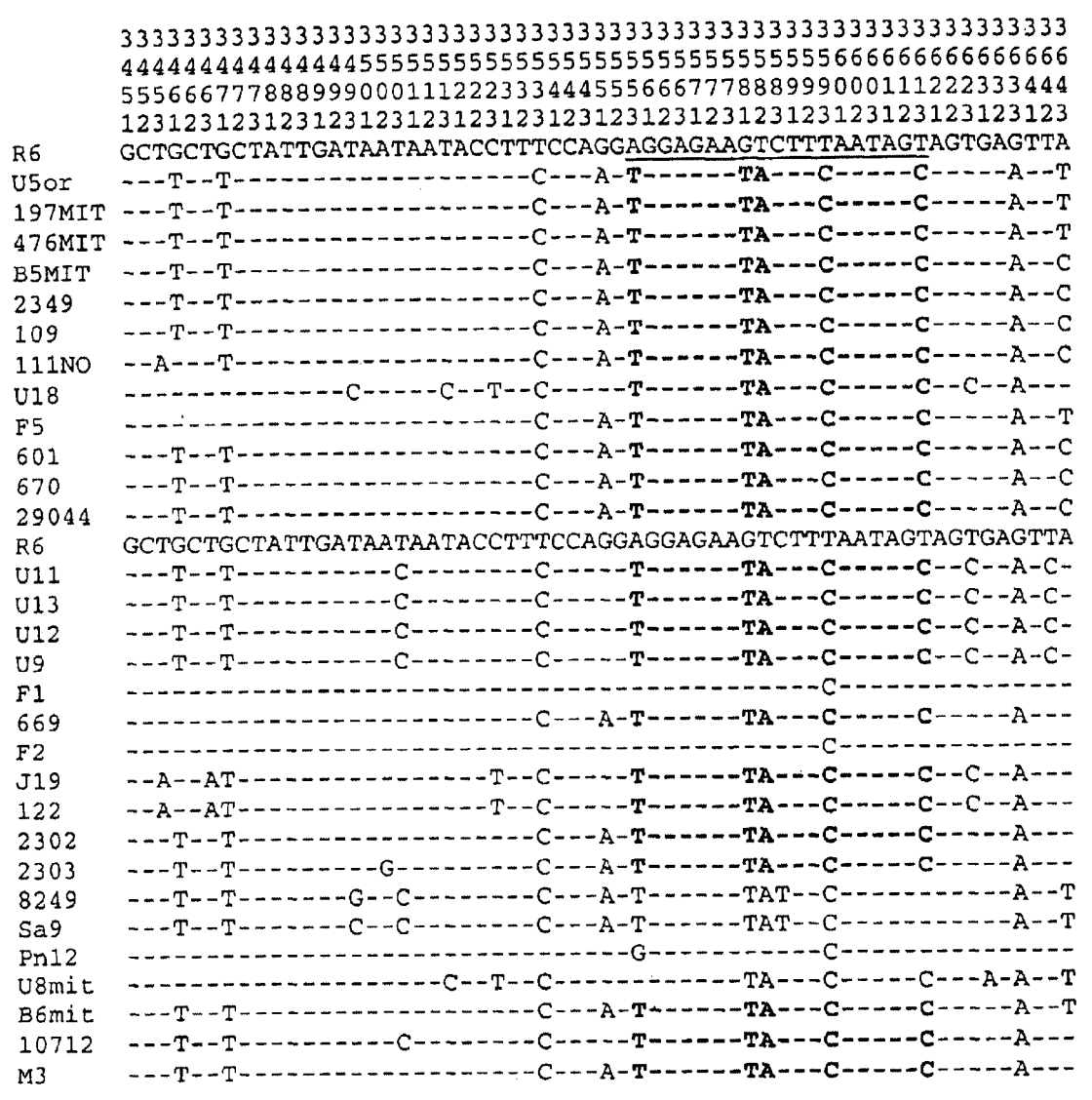
Figure 4Q:
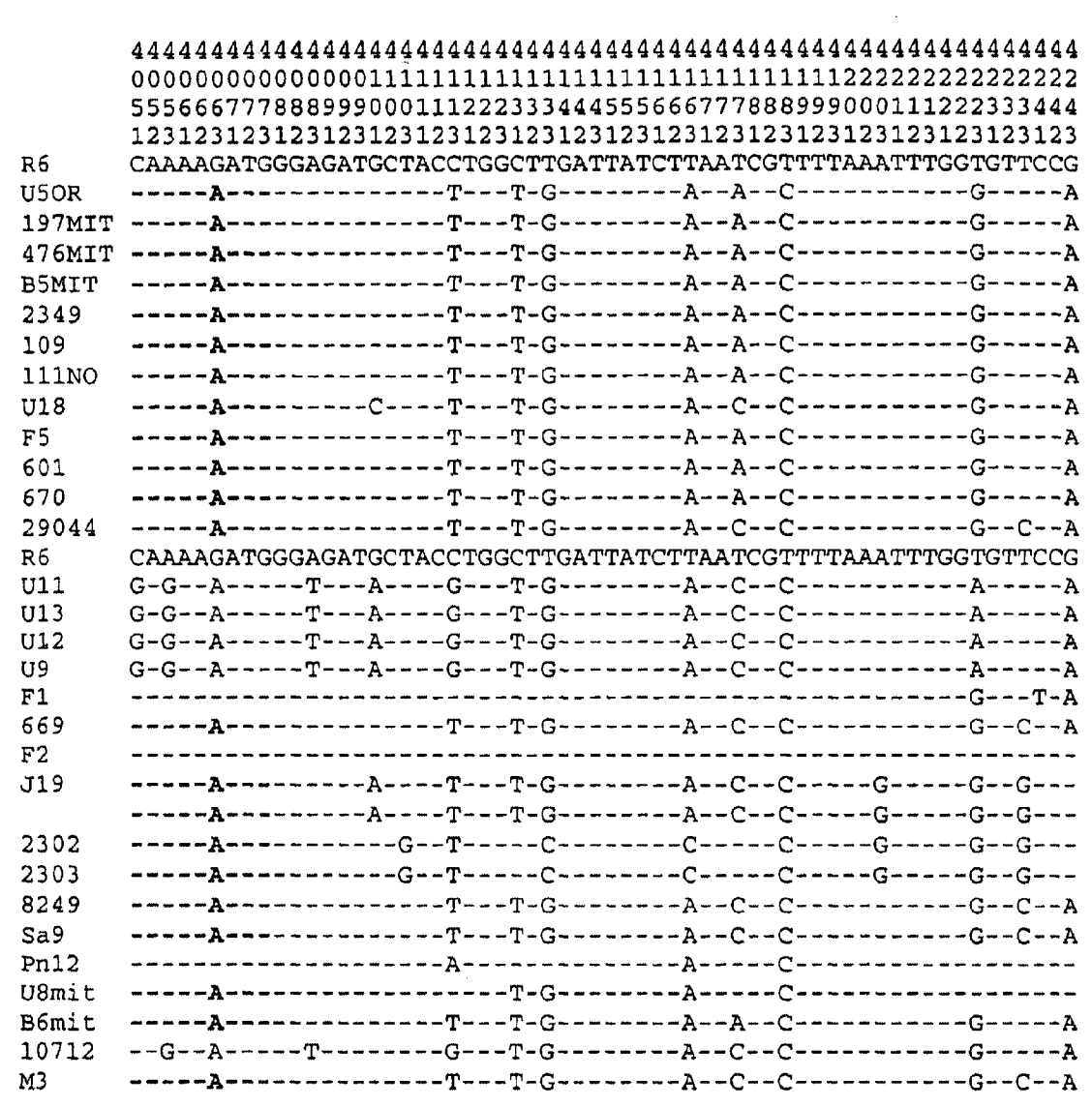
Figure 4R:
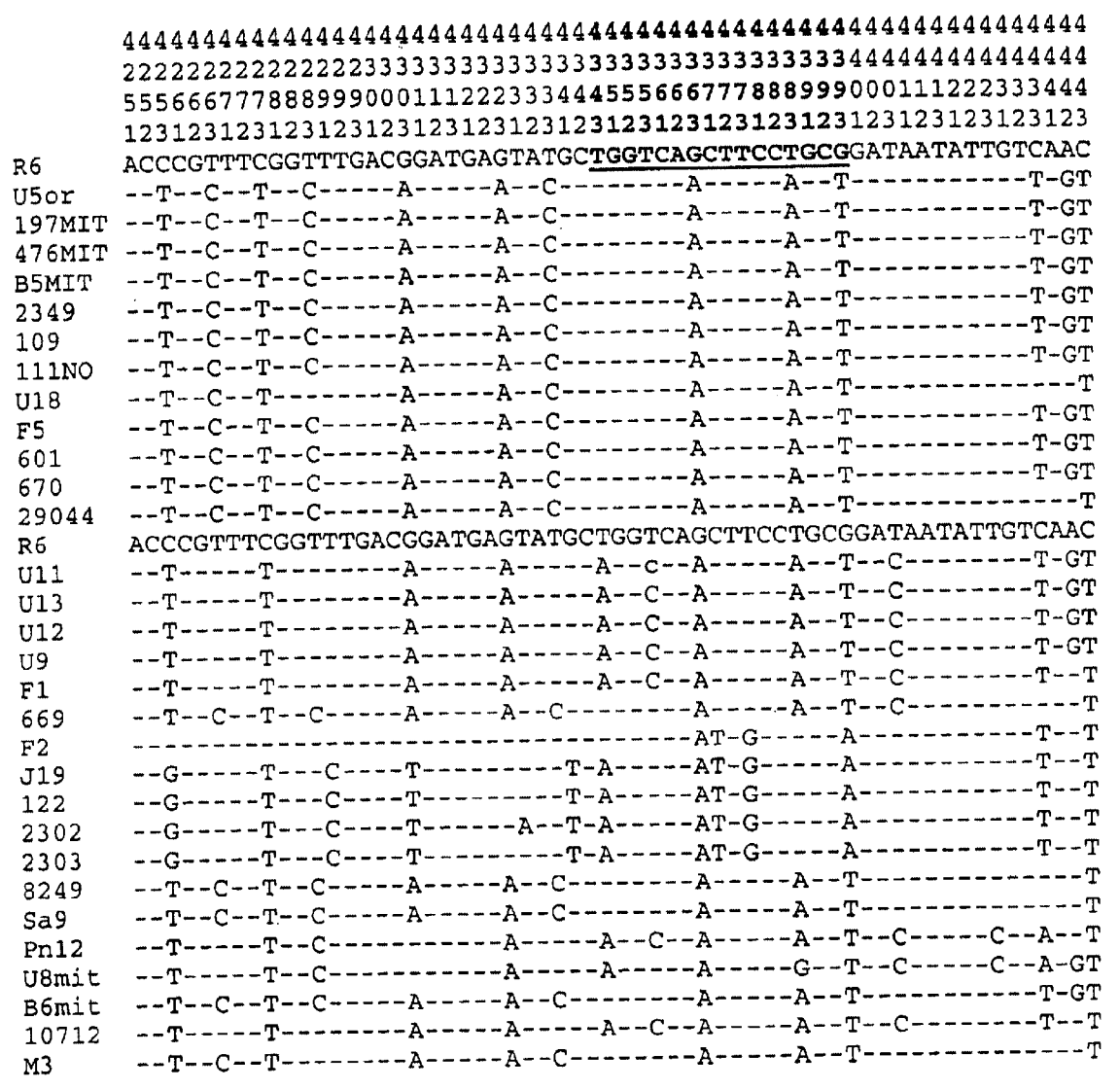
Figure 4S:
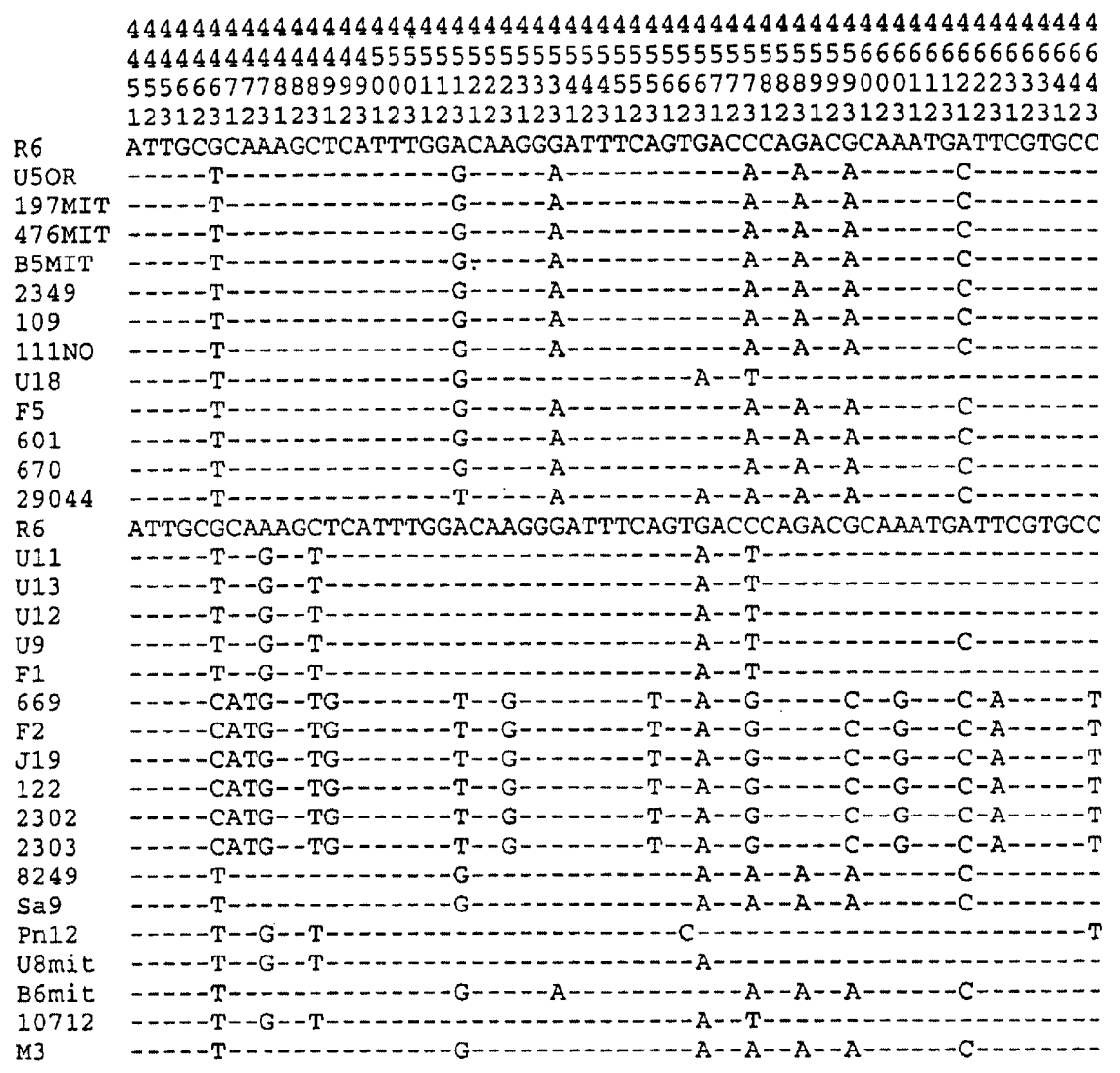
Figure 4U:
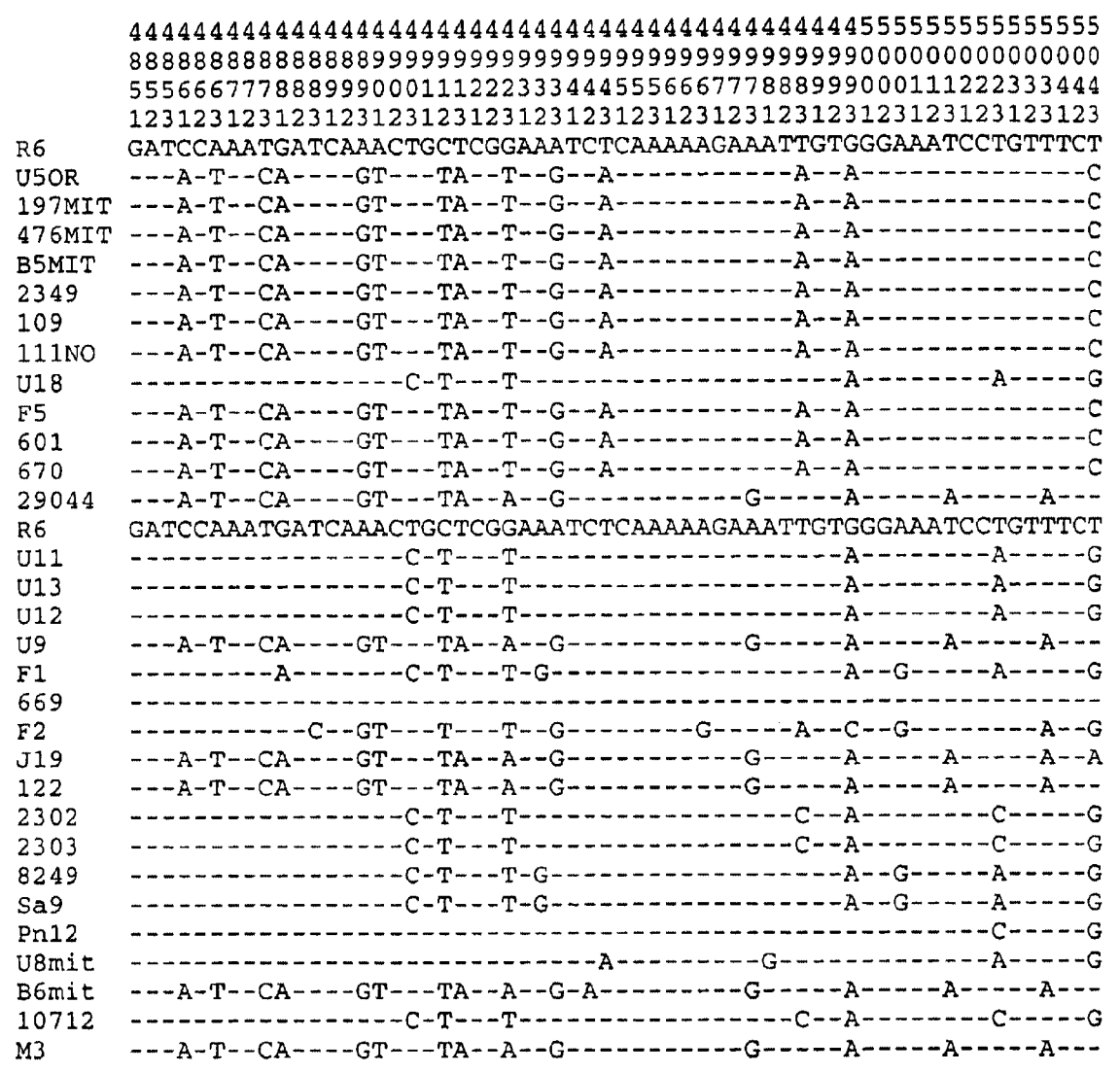
Figure 4W:
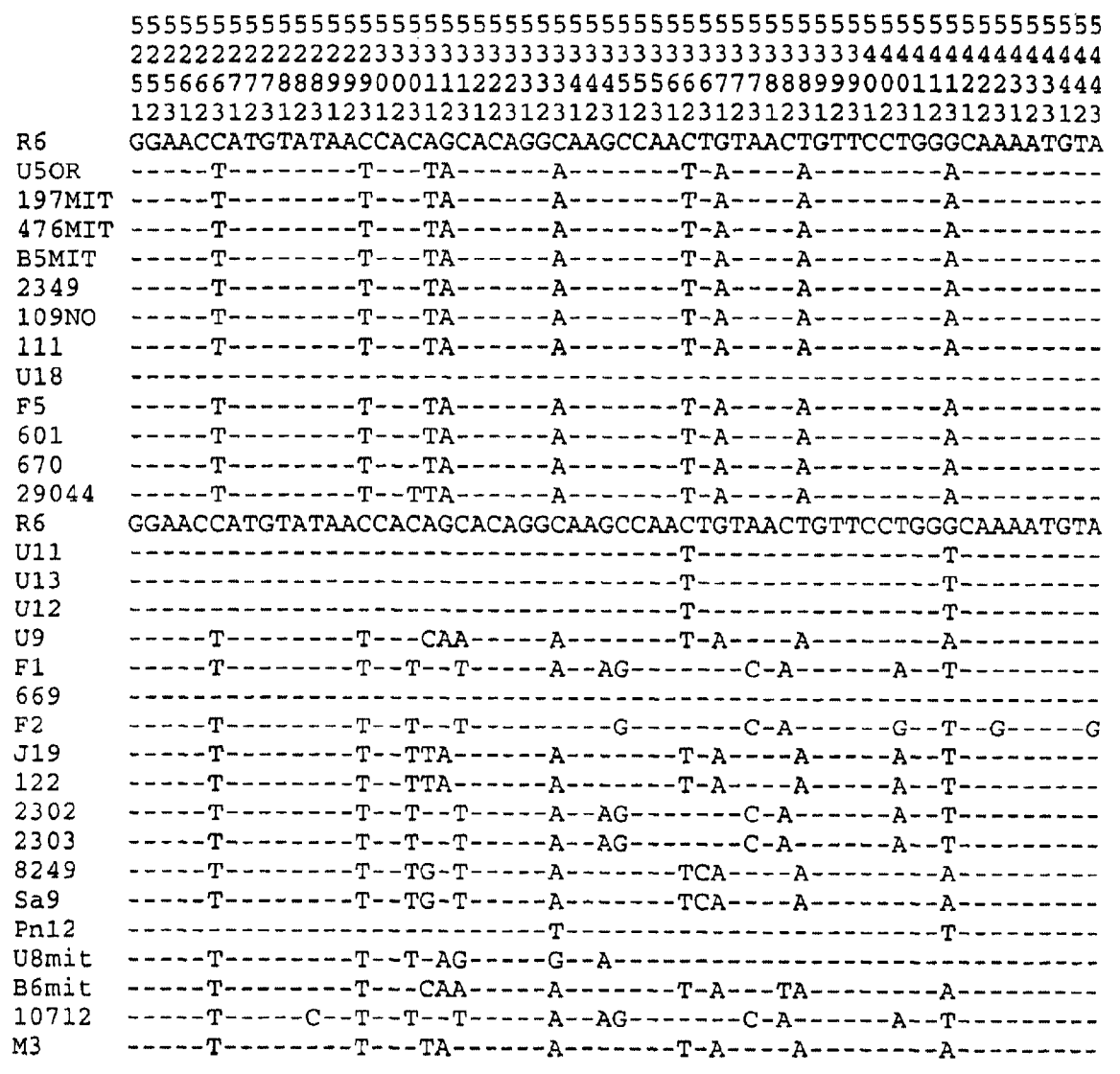
Figure 4X:
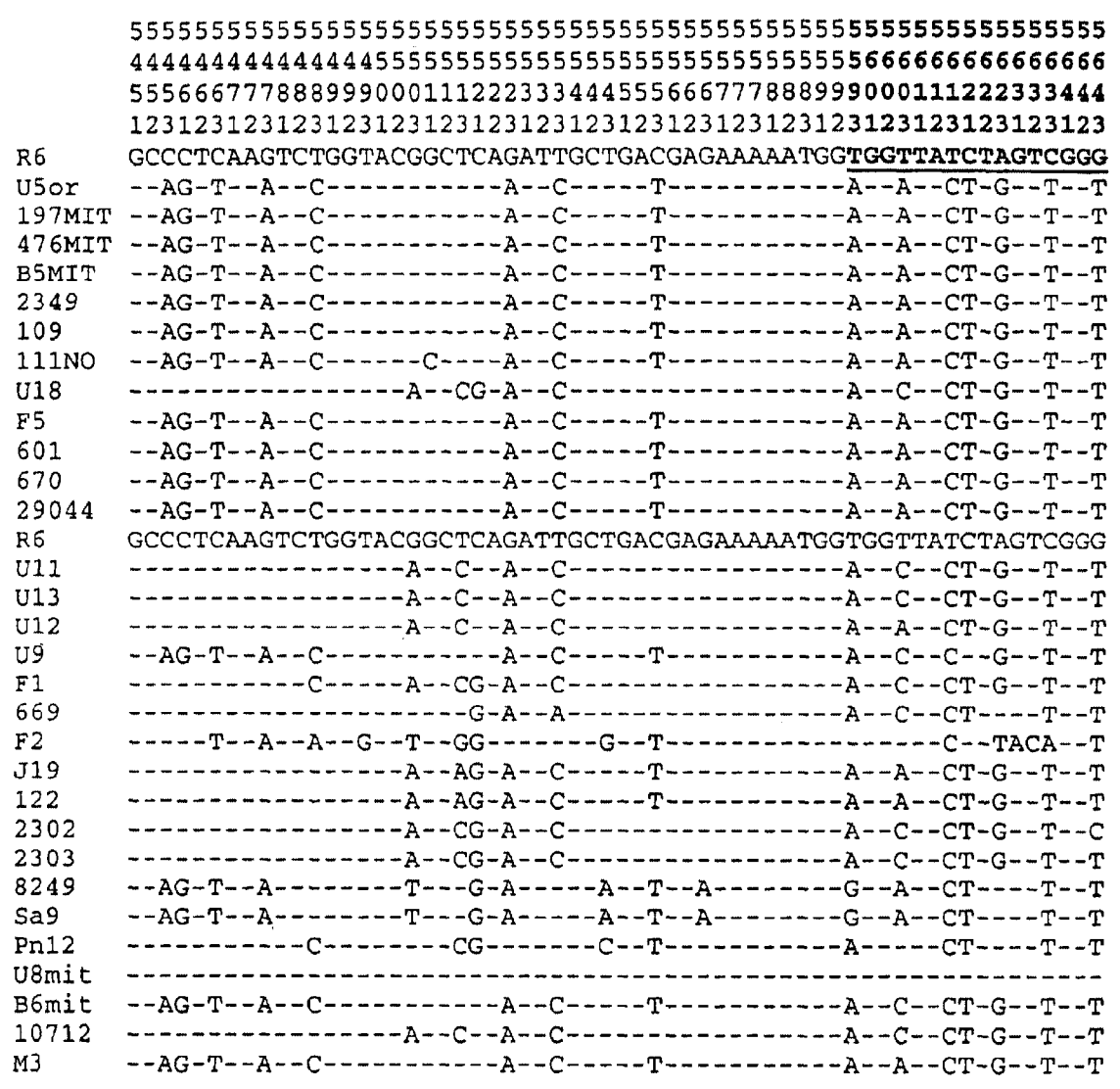
Figure 4Z:
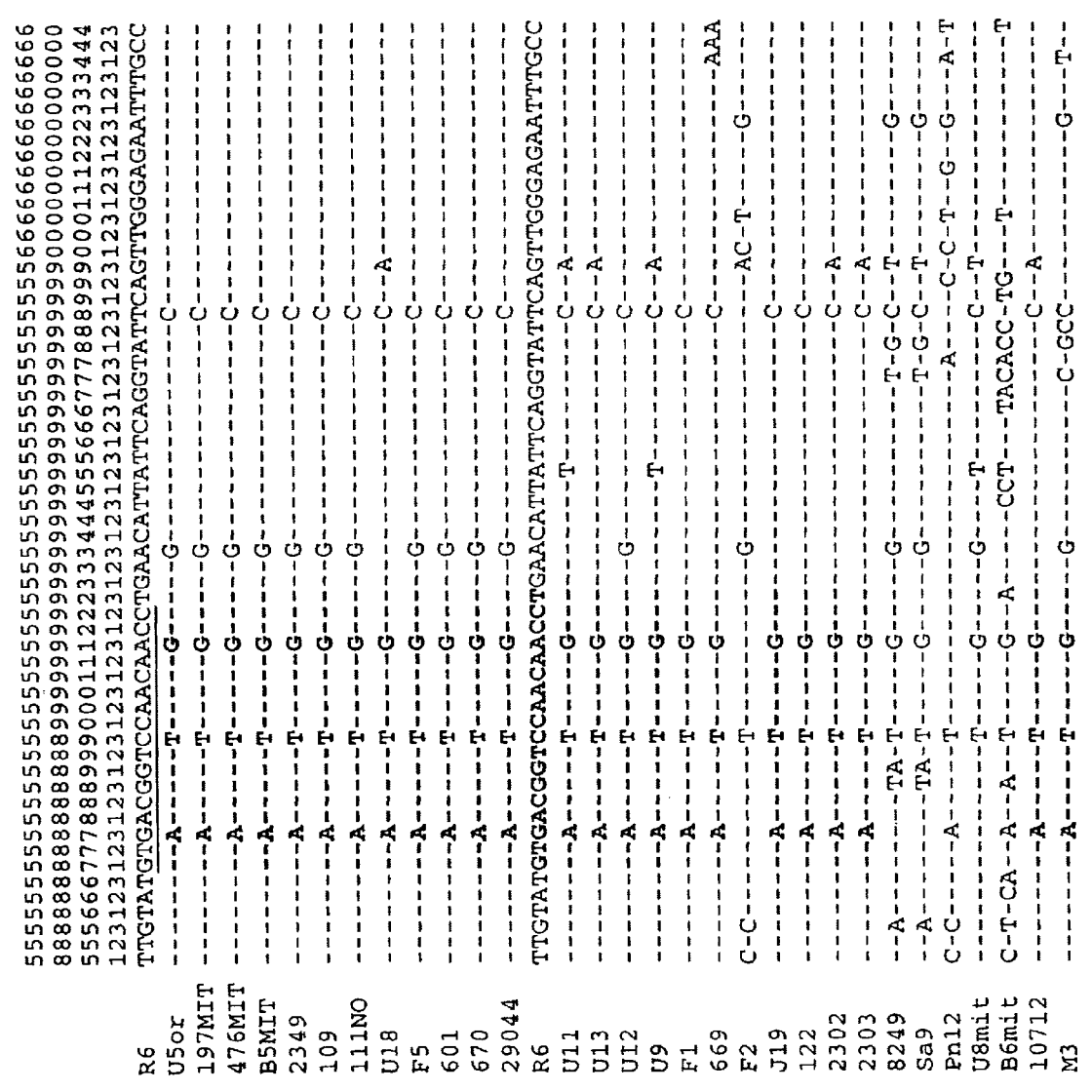

FIG. 4 (A–HH) Detection of the probes according to the invention by sequence comparisons.

The invention is further described by means of an example.

EXAMPLE

Isolation of S. pneumoniae Bacterial DNA and Subsequent Testing for Existing Resistance to Penicillin Bacteria of the strain S. pneumoniae R6 are inoculated in brain-heart infusion (BHI) broth and allowed to grow at 37° C. overnight. The cells were centrifuged off and lyzed by, resuspension of the sediment in 10 µl of 10 mM Tris/HCl buffer, pH 7.2, 0.05% triton-X100. 1 µl of the cell suspension each are used per 20 µl PCR batch (0.2 µl Taq polymerase, 1 pM oligonucleotide primer each, 2 µl 10×PCR buffer, 4–6 mM MgCl$_2$). 25 cycles with 5 seconds of annealing at 96° C., 5 seconds of annealing at 52° C., 10 seconds of extension at 72° C. suffice for the PCR reaction.

A) Agarose Gel Electrophoresis

The following primer combinations are used in the PCR reactions (conditions see above):

| Forward primers | reverse primers |
| --- | --- |
| probe (1) | probe (8) |
| probe (2) | probe (8) |
| probe (3) | probe (8) |
| probe (4) | probe (8) |
| probe (5) | probe (8) |
| probe (6) | probe (8) |
| probe (7) | probe (8) |
| probe (I) | probe (IV) |
| probe (II) | probe (IV) |

The designations of the probes correspond to the numerals for PBP2x, indicated above in connection with the sequences.

In each case, 4 µl aliquots of the PCR reactions were applied onto a 1.5% agarose gel and separated electrophoretically. The result is shown in FIG. 3. It follows therefrom that R6 is a sensitive strain.

B1) Dot Blot

S. pneumoniae R6 bacterial DNA is amplified with common primers (Grebe and Hakenbeck (1996), Antimicrob. Agents Chemotherap. 40, pp. 829–834) in a PCR reaction (conditions see above). The PCR-amplified DNA is denatured by heating (2 min. at 96° C., then 4° C.)., 2 µl thereof each are applied per sample onto a nylon membrane. The DNA is fixed by irradiation with long-wave U.V. light onto the membrane, and non-specific binding sites are saturated at 60° C. in prehybridization solution (6×SSC, 5×Denhardt solution, 0.1% SDS, 50 mM Na phoshphate buffer, pH 6.5, 0.1 mg/ml heringsperm DNA) with mild shaking for 5 hours. The hybridization with the PBP2x sensitivity-specific oligonucleotide probes (1) to (8) and the resistance-specific probes (I) to (IV), respectively, is carried out in hybridization buffer (like prehybridization solution but with 50 ng/ml oligonucleotide probe) at about 50° C. overnight. The filter is washed at room temperature with 2×SSC/0.1% SDS at 55° C. for 2×5 minutes. The samples are stained using anti-DIG-AP conjugate in accordance with the instructions from the manufacturer (Boehringer Mannheim). Here, it also turns out that only the sensitivity-specific probes result in a hybridization, which indicates that the S. pneumoniae strain R6 is a penicillin-sensitive strain.

B2) Oligonucleotide Microarray

The method is carried out as defined above under B1) but with the difference that the oligonucleotides are offered as finished array and the DNA to be hybridized must be labeled via PCR by means of DIG or fluorescein-labeled nucleotides. The principle of high-density microarray hybridization is described in "Nature Biotechnology 14, pages 1675–1680, 1996". The result of this experiment is shown in FIG. 2A.

What is claimed is:

1. A method for testing *Streptococcus pneumoniae* for resistance to penicillin, the method comprising the steps of:
   a) isolating DNA from a *Streptococcus pneumoniae* strain,
   b) hybridizing the DNA obtained in step (a) with at least one sensitivity-specific DNA probe and at least one resistance-specific DNA probe, and
   c) determining whether or not said *Streptococcus pneumoniae* strain is sensitive to penicillin or not by detecting which probe or probes hybridize.
   wherein the sensitivity-specific probes are selected from the group of sequences consisting of SEQ ID NO: 1, SEQ ID NO: 2, SEQ ID NO: 3, SEQ ID NO: 4, SEQ ID NO: 5, SEQ ID NO: 6 and sequences which differ from said sequences by one to four nucicotides, wherein SEQ ID NOS.: 1–6 are, respectively:

AGT CAG CAA CGG GTA AG,

AAC GAA CGA TGG ACG GT,

CAT TTC CAG NCC CCT CCA,

TGC AGA TGC CAC GAT TC,

CTG GTC AGC TTC CTG CG, and

TGG TTA TCT AGT CGG GTT AA;

wherein N is any nucleotide.

2. A method for testing *Streptococcus pneumoniae* for resistance to, penicillin the method comprising the steps of:
   a) isolating DNA from a *Streptococcus pneumoniae* strain
   b) hybridizing the DNA obtained in step (a) with at least one sensitivity-specific DNA probe and at least one resistance-specific DNA probe, and
   c) determining whether or not said *Streptococcus pneumoniae* strain is sensitive to penicillin or not by detecting which probe or probes hybridize,
   wherein the resistance-specific probes are selected from the group of sequences consisting of SEQ ID NO: 14, SEQ ID NO: 15, SEQ ID NO: 16, SEQ ID NO: 17, and sequences which differ from said sequences by one to four nucleotides, wherein SEQ ID NOS.: 14–17 are, respectively:

TGG AGA ATA NTT CAA TAG N,

GTC TAC TTG AAC AAA AAA TG,

TTA GTT GGG ACG GAC CCT, and

GTA ACN NTT CAA CAG CCT;

wherein N is any nucleotide.

3. The method according to claims 1, wherein the probes are labeled radioactively.

4. A method for testing *Streptococcus pneumoniae* for resistance to penicillin, the method comprising the steps of:
   a) isolating DNA from a *Streptococcus pneumonia* strain,
   b) hybridizing the DNA obtained in step (a) with at least one sensitivity-specific DNA probe and at least one resistance-specific DNA probe, and
   c) determining whether or not said *Streptococcus pneumoniae* strain is sensitive to penicillin or not by detecting which probe or probes hybridize;

wherein the sensitivity-specific probes are probes which specifically hybridize to the DNA of antibiotic sensitive strains and are selected from the group of sequences consisting of SEQ ID NO: 1, SEQ ID NO: 2, SEQ ID NO: 3, SEQ ID NO: 4, SEQ ID NO: 5, SEQ ID NO: 6 and sequences which differ from said sequences by one to four nucleotides wherein SEQ ID NOS.:1–6 are, respectively:

```
AGT CAG CAA CGG GTA AG,
AAC GAA CGA TGG ACG GT,
CAT TTC CAG NCC CCT CCA,
TGC AGA TGC CAC GAT TC,
CTG GTC AGC TTC CTG CG, and
TGG TTA TCT AGT CGG GTT AA;
``` wherein N is any nucleotide; and wherein the resistance-specific probes are probes which specifically hybridize to the DNA of antibiotic resistant strains and are selected from the group of sequences consisting of SEQ ID NO: 14, SEQ ID NO: 15, SEQ ID NO: 16, SEQ ID NO: 17, and sequences which differ from said sequences by one to four nucleotides wherein SEQ ID NOS.:14–17 are, respectively:

```
TGG AGA ATA NTT CAA TAG N,
GTC TAC TTG AAC AAA AAA TG,
TTA GTT GGG ACG GAC CCT, and
GTA ACN NTT CAA CAG CCT;
``` wherein N is any nucleotide.

5. A method for testing *Streptococcus pneumoniae* for resistance to penicillin, the method comprising the steps of:
a) isolating DNA from a *Streptococcus pneumonia* strain,
b) hybridizing the DNA obtained in step (a) with at least one sensitivity-specific DNA probe and at least one resistance-specific DNA probe, and
c) determining whether or not said *Streptococcus pneumoniae* strain is sensitive to penicillin or not by detecting which probe or probes hybridize;
wherein the sensitivity-specific probes are probes which specifically hybridize to the DNA of antibiotic sensitive strains and are selected from the group of sequences consisting of SEQ ID NO: 1, SEQ ID NO: 2, SEQ ID NO: 3, SEQ ID NO: 4, SEQ ID NO: 5 and SEQ ID NO: 6, wherein SEQ ID NOS.:1–6 are, respectively:

```
AGT CAG CAA CGG GTA AG,
AAC GAA CGA TGG ACG GT,
CAT TTC CAG NCC CCT CCA,
TGC AGA TGC CAC GAT TC,
CTG GTC AGC TTC CTG CG, and
TGG TTA TCT AGT CGG GTT AA;
``` wherein N is any nucleotide; and wherein the resistance-specific probes are probes which specifically hybridize to the DNA of antibiotic resistant strains and are selected from the group of sequences consisting of SEQ ID NO: 14, SEQ ID NO: 15, SEQ ID NO: 16 and SEQ ID NO: 17, wherein SEQ ID NOS.:14–17 are, respectively:

```
TGG AGA ATA NTT CAA TAG N,
GTC TAC TTG AAC AAA AAA TG,
TTA GTT GGG ACG GAC CCT, and
GTA ACN NTT CAA CAG CCT;
``` wherein N is any nucleotide.

6. The method of claim 4, wherein the DNA isolated in step (a) is obtained from a strain of bacteria having unknown antibiotic sensitivity or resistance.

7. The method of claim 6, wherein step (b) is performed at least a second time, thereby hybridizing the DNA obtained in step (a) with at least a second different sensitivity-specific DNA probe and at least a second different resistance-specific DNA probe.

8. The method of claim 5, wherein the DNA isolated in step (a) is obtained from a strain bacteria strain having unknown antibiotic sensitivity or resistance.

9. The method of claim 8, wherein step (b) is performed at least a second time, thereby hybridizing the DNA obtained in step (a) with at least a second different sensitivity-specific DNA probe and at least a second different resistance-specific DNA probe.

10. The method of claim 1, wherein the DNA isolated in step (a) is obtained from a strain of *Streptococcus pneumoniae* having unknown penicillin sensitivity or resistance.

11. The method according to claim 2, wherein the probes are labeled radioactively.

12. The method of claim 2, wherein the DNA isolated in step (a) is obtained from a strain of *Streptococcus pneumoniae* having unknown penicillin sensitivity or resistance.

* * * * *

SEQUENCE LISTING

<160> NUMBER OF SEQ ID NOS: 25

<210> SEQ ID NO 1
<211> LENGTH: 17
<212> TYPE: DNA
<213> ORGANISM: Streptococcus pneumoniae

<400> SEQUENCE: 1
agtcagcaac gggtaag                                                  17

<210> SEQ ID NO 2
<211> LENGTH: 17
<212> TYPE: DNA
<213> ORGANISM: Streptococcus pneumoniae

<400> SEQUENCE: 2
aacgaacgat ggacggt                                                  17

<210> SEQ ID NO 3
<211> LENGTH: 18
<212> TYPE: DNA
<213> ORGANISM: Streptococcus pneumoniae
<220> FEATURE:
<221> NAME/KEY: misc_feature
<222> LOCATION: (10)
<223> OTHER INFORMATION: Nucleotide at position 10 is n wherein n
      is any nucleotide but preferably c.

<400> SEQUENCE: 3
catttccagn cccctcca                                                 18

<210> SEQ ID NO 4
<211> LENGTH: 17
<212> TYPE: DNA
<213> ORGANISM: Streptococcus pneumoniae

<400> SEQUENCE: 4
tgcagatgcc acgattc                                                  17

<210> SEQ ID NO 5
<211> LENGTH: 17
<212> TYPE: DNA
<213> ORGANISM: Streptococcus pneumoniae

<400> SEQUENCE: 5
ctggtcagct tcctgcg                                                  17

<210> SEQ ID NO 6
<211> LENGTH: 20
<212> TYPE: DNA
<213> ORGANISM: Streptococcus pneumoniae

<400> SEQUENCE: 6
tggttatcta gtcgggttaa                                               20

<210> SEQ ID NO 7
<211> LENGTH: 17
<212> TYPE: DNA
<213> ORGANISM: Streptococcus pneumoniae

<400> SEQUENCE: 7
ctgtatcgat gagtccg                                                  17

```
<210> SEQ ID NO 8
<211> LENGTH: 19
<212> TYPE: DNA
<213> ORGANISM: Streptococcus pneumoniae

<400> SEQUENCE: 8
aacagttctg ctgaagaag                                                  19

<210> SEQ ID NO 9
<211> LENGTH: 18
<212> TYPE: DNA
<213> ORGANISM: Streptococcus pneumoniae

<400> SEQUENCE: 9
taggagcacg ccatcagt                                                   18

<210> SEQ ID NO 10
<211> LENGTH: 18
<212> TYPE: DNA
<213> ORGANISM: Streptococcus pneumoniae

<400> SEQUENCE: 10
gacgaaatgc ctatcttg                                                   18

<210> SEQ ID NO 11
<211> LENGTH: 19
<212> TYPE: DNA
<213> ORGANISM: Streptococcus pneumoniae

<400> SEQUENCE: 11
ctctcaattt gtagcacct                                                  19

<210> SEQ ID NO 12
<211> LENGTH: 19
<212> TYPE: DNA
<213> ORGANISM: Streptococcus pneumoniae

<400> SEQUENCE: 12
ctattctaac cgtctgaca                                                  19

<210> SEQ ID NO 13
<211> LENGTH: 20
<212> TYPE: DNA
<213> ORGANISM: Streptococcus pneumoniae

<400> SEQUENCE: 13
atcaaatacc tatatggtcc                                                 20

<210> SEQ ID NO 14
<211> LENGTH: 19
<212> TYPE: DNA
<213> ORGANISM: Streptococcus pneumoniae
<220> FEATURE:
<221> NAME/KEY: misc_feature
<222> LOCATION: (10)..(19)
<223> OTHER INFORMATION: Nucleotides at positions 10 and 19 are n
      wherein n is any nucleotide but preferably c.

<400> SEQUENCE: 14
tggagaatan ttcaatagn                                                  19

<210> SEQ ID NO 15
<211> LENGTH: 20
<212> TYPE: DNA
<213> ORGANISM: Streptococcus pneumoniae
```

-continued

```
<400> SEQUENCE: 15
gtctacttga acaaaaaatg                                               20

<210> SEQ ID NO 16
<211> LENGTH: 18
<212> TYPE: DNA
<213> ORGANISM: Streptococcus pneumoniae

<400> SEQUENCE: 16
ttagttggga cggaccct                                                 18

<210> SEQ ID NO 17
<211> LENGTH: 18
<212> TYPE: DNA
<213> ORGANISM: Streptococcus pneumoniae
<220> FEATURE:
<221> NAME/KEY: misc_feature
<222> LOCATION: (6)..(7)
<223> OTHER INFORMATION: Nucleotides at positions 6 and 7 are n
      wherein n is any nucleotide but preferably g.

<400> SEQUENCE: 17
gtaacnnttc aacagcct                                                 18

<210> SEQ ID NO 18
<211> LENGTH: 19
<212> TYPE: DNA
<213> ORGANISM: Streptococcus pneumoniae
<220> FEATURE:
<221> NAME/KEY: misc_feature
<222> LOCATION: (7)
<223> OTHER INFORMATION: Nucleotide at position 7 is n wherein n
      is any nucleotide but preferably t.

<400> SEQUENCE: 18
ctccgancaa tacgtctct                                                19

<210> SEQ ID NO 19
<211> LENGTH: 20
<212> TYPE: DNA
<213> ORGANISM: Streptococcus pneumoniae
<220> FEATURE:
<221> NAME/KEY: misc_feature
<222> LOCATION: (10)
<223> OTHER INFORMATION: Nucleotide at position 10 is n wherein n
      is any nucleotide but preferably g.

<400> SEQUENCE: 19
gctccagatn aaatgtttgt                                               20

<210> SEQ ID NO 20
<211> LENGTH: 19
<212> TYPE: DNA
<213> ORGANISM: Streptococcus pneumoniae

<400> SEQUENCE: 20
aggagaagtc tttaatagt                                                19

<210> SEQ ID NO 21
<211> LENGTH: 20
<212> TYPE: DNA
<213> ORGANISM: Streptococcus pneumoniae

<400> SEQUENCE: 21
ccctccttga gcaaaagatg                                               20
```

```
<210> SEQ ID NO 22
<211> LENGTH: 18
<212> TYPE: DNA
<213> ORGANISM: Streptococcus pneumoniae

<400> SEQUENCE: 22
ttggtaggga cggatccg                                                 18

<210> SEQ ID NO 23
<211> LENGTH: 18
<212> TYPE: DNA
<213> ORGANISM: Streptococcus pneumoniae

<400> SEQUENCE: 23
gtgacggtcc aacaacct                                                 18

<210> SEQ ID NO 24
<211> LENGTH: 19
<212> TYPE: DNA
<213> ORGANISM: Streptococcus pneumoniae

<400> SEQUENCE: 24
tacagacgaa tacgttgcc                                                19

<210> SEQ ID NO 25
<211> LENGTH: 20
<212> TYPE: DNA
<213> ORGANISM: Streptococcus pneumoniae

<400> SEQUENCE: 25
gcacctgatg aactatttgc                                               20
```